US00RE50235E

(19) United States
(12) Reissued Patent
Rado

(10) Patent Number: US RE50,235 E
(45) Date of Reissued Patent: *Dec. 10, 2024

(54) PERSONAL VAPORIZER HAVING REVERSING AIR FLOW

(71) Applicant: LUBBY HOLDINGS, LLC, Torrance, CA (US)

(72) Inventor: J. Christian Rado, Torrance, CA (US)

(73) Assignee: Lubby Holdings, LLC, Torrance, CA (US)

( * ) Notice: This patent is subject to a terminal disclaimer.

(21) Appl. No.: 18/127,621

(22) Filed: Mar. 28, 2023

Related U.S. Patent Documents

Reissue of:
(64) Patent No.: 10,188,145
Issued: Jan. 29, 2019
Appl. No.: 15/276,712
Filed: Sep. 26, 2016

U.S. Applications:
(63) Continuation of application No. 17/163,338, filed on Apr. 20, 2021, now Pat. No. Re. 49,473, which is an application for the reissue of Pat. No. 10,188,145.

(60) Provisional application No. 62/232,691, filed on Sep. 25, 2015.

(51) Int. Cl.

| | |
|---|---|
| ***A61M 15/06*** | (2006.01) |
| ***A24F 40/20*** | (2020.01) |
| ***A24F 40/485*** | (2020.01) |
| ***H05B 1/02*** | (2006.01) |

(52) U.S. Cl.
CPC ..... *H05B 1/0227* (2013.01); *A24F 40/485* (2020.01); *A61M 15/06* (2013.01); *A24F 40/20* (2020.01)

(58) Field of Classification Search
CPC ..... A24F 40/20; A24F 40/485; A61M 15/06; H05B 1/0227
See application file for complete search history.

(56) References Cited

U.S. PATENT DOCUMENTS

| | | | | |
|---|---|---|---|---|
| 2,104,266 A | | 9/1935 | McCormick | |
| 4,036,240 A | * | 7/1977 | Murray, Jr. | A24F 1/30 131/176 |
| 4,947,874 A | | 8/1990 | Brooks et al. | |

(Continued)

FOREIGN PATENT DOCUMENTS

| | | |
|---|---|---|
| KR | 20130106009 A | 9/2013 |
| WO | WO2014012907 A1 | 1/2014 |

OTHER PUBLICATIONS

International Search Report from USPTO dated Dec. 7, 2016 for related International Application No. PCT/US2016/053829.

(Continued)

*Primary Examiner* — William E Dondero
(74) *Attorney, Agent, or Firm* — FisherBroyles, LLC; Glen L Nuttall

(57) ABSTRACT

A personal vaporizer has an atomizer module having a heating element and an atomizer cup for receiving vaporizing medium. A flow module is releasably attached to the atomizer module. The flow module intakes ambient air and directs the air into a vaporizing chamber at and adjacent the atomizer cup, where the air mixes with atomized medium to form a vapor. The vapor exits the vaporizing chamber via one or more exit passages defined through the flow module. Vapor is directed from the exit passages into a mouthpiece and further into the user's mouth.

19 Claims, 18 Drawing Sheets

(56) References Cited

U.S. PATENT DOCUMENTS

| | | | | |
|---|---|---|---|---|
| 6,532,965 | B1 * | 3/2003 | Abhulimen | A24F 47/004 131/175 |
| 6,543,448 | B1 * | 4/2003 | Smith | A61M 15/0045 128/203.15 |
| 7,997,280 | B2 * | 8/2011 | Rosenthal | A61M 11/041 128/202.21 |
| 8,156,944 | B2 | 4/2012 | Han | |
| 8,365,742 | B2 | 2/2013 | Hon | |
| 8,424,537 | B2 * | 4/2013 | Rosenthal | A61M 11/041 131/191 |
| 8,794,231 | B2 | 8/2014 | Thorens et al. | |
| 8,899,238 | B2 | 12/2014 | Robinson et al. | |
| 8,910,639 | B2 | 12/2014 | Chang et al. | |
| 8,997,753 | B2 * | 4/2015 | Li | H01C 17/00 128/202.21 |
| 9,380,811 | B2 | 7/2016 | Chung | |
| 9,462,832 | B2 | 10/2016 | Lord | |
| 9,750,284 | B2 | 9/2017 | Rado | |
| 10,188,145 | B2 | 1/2019 | Rado | |
| 10,219,541 | B2 | 3/2019 | Rado | |
| 10,244,792 | B2 | 4/2019 | Rado | |
| 10,321,721 | B2 | 6/2019 | Rado | |
| 10,327,470 | B2 | 6/2019 | Rado | |
| 10,517,334 | B1 | 12/2019 | Volodarsky et al. | |
| RE49,473 | E * | 3/2023 | Rado | A24F 40/485 239/77 |
| 2005/0051182 | A1 | 3/2005 | Hcu | |
| 2006/0110144 | A1 | 5/2006 | Fellows | |
| 2009/0293888 | A1 | 12/2009 | Williams et al. | |
| 2010/0147292 | A1 | 6/2010 | Hamaguchi et al. | |
| 2011/0036346 | A1 * | 2/2011 | Cohen | A61M 15/0065 128/200.14 |
| 2011/0061649 | A1 | 3/2011 | Hirshberg | |
| 2011/0094523 | A1 | 4/2011 | Thorens et al. | |
| 2011/0259972 | A1 | 10/2011 | Rosenthal | |
| 2013/0152922 | A1 * | 6/2013 | Benassayag | A61M 15/06 128/202.21 |
| 2013/0247910 | A1 | 9/2013 | Postma | |
| 2013/0298905 | A1 | 11/2013 | Levin et al. | |
| 2014/0041655 | A1 | 2/2014 | Barron et al. | |
| 2014/0174458 | A1 | 6/2014 | Katz | |
| 2015/0117842 | A1 | 4/2015 | Brammer et al. | |
| 2015/0136158 | A1 | 5/2015 | Stevens et al. | |
| 2015/0208729 | A1 | 7/2015 | Monsees et al. | |
| 2015/0208730 | A1 * | 7/2015 | Li | A61M 15/06 131/329 |
| 2015/0245662 | A1 | 9/2015 | Memari et al. | |
| 2015/0258288 | A1 * | 9/2015 | Sullivan | A61M 15/0086 128/203.12 |
| 2015/0282524 | A1 | 10/2015 | Elhalwani | |
| 2016/0295919 | A1 | 10/2016 | Thomas, Jr. | |
| 2017/0055579 | A1 | 3/2017 | Kuna et al. | |
| 2017/0354186 | A1 | 12/2017 | Johnson et al. | |
| 2019/0021395 | A1 | 1/2019 | Qiu | |

OTHER PUBLICATIONS

International Preliminary Report on Patentability from the International Bureau of WIPO dated Apr. 5, 2018 for related International Application No. PCT/US2016/053829.

* cited by examiner

PERSONAL VAPORIZER HAVING REVERSING AIR FLOW

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[The] *This* application *is a continuation reissue of U.S. application Ser. No. 17/163,338, filed on Apr. 20, 2021, now RE49,473, which is an application for reissue of U.S. Pat. No. 10,188,145 which* claims priority to U.S. Provisional Application No. 62/232,691, which was filed on Sep. 25, 2015, the entirety of *each of* which [is] *are* hereby incorporated by reference *herein*.

BACKGROUND

The present disclosure relates to the field of personal vaporizers.

Personal vaporizers are handheld devices that can vaporize a vaporizing medium, which vapor is then inhaled by its user. The vaporization medium can be in the form of a liquid solution or wax, and can include one or more of various essential oils, such as cannabis oil. The medium can also include other ingredients such as extracted flavorings or scents. Personal vaporizers for vaporizing a liquid typically include a chamber that holds the liquid solution. The liquid solution is configured to produce the vapor when heated by the atomizer, and typically includes chemicals such as one or more of propylene glycol, glycerin, polyethylene glycol 400, cannabis oil, other essential oils, and/or an alcohol. Extracted flavorings can also be included in the solution. Electronic cigarettes are a type of personal vaporizer, and use a liquid solution that often includes tobacco-derived nicotine.

Personal vaporizers include an atomizer that has a heating element that selectively heats the medium in order to atomize the medium. A user sucks on a mouthpiece of the vaporizer to draw atmospheric air into and through the atomizer, where it is mixed with atomized medium to form a vapor, which is then drawn through the mouthpiece by the user. Air flow through a vaporizer must be managed in order to obtain optimal vaporization of the medium.

SUMMARY

There is a need in the art for a personal vaporizer that directs intake air into and through an atomizer of the vaporizer so as to mix air with atomized media in order to obtain a high-quality vapor. There is a further need in the art for a personal vaporizer configured so that the flow of intake air changes flow direction in the atomizer.

In accordance with some embodiments, the present specification provides a personal vaporizer having an atomizer module comprising an atomizer cup having a distal wall and a side wall extending from the distal wall to a proximal edge. A heating element is arranged in or adjacent the atomizer cup, and the cup is configured to accept a vaporizing medium and to atomize the vaporizing medium when the heating element is energized. A vaporizing chamber is defined in part by the distal and side walls of the atomizer cup. A flow body is selectively attachable to the atomizer module. The flow module comprises an inlet passage through a side of the flow body. The inlet passage communicates with a delivery passage that extends distally to a delivery opening, The delivery opening is configured to direct intake air into the vaporizing chamber. An exit passage communicates with the vaporizing chamber and extends through the flow module. An exit opening communicates with the exit passage and is radially spaced from the delivery opening. A vaporizing chamber flow path is defined between the delivery opening and the exit passage, and atomized vaporizing medium becomes entrained in the air flowing along the vaporizing chamber flow path so as to form a vapor.

In some embodiments, the vaporizing chamber flow path changes direction by 180° between the delivery opening and the exit opening. In further embodiments the delivery opening is distal of the exit opening. In still further embodiments, a cross-sectional area of the delivery opening is less than a cross-sectional area of the inlet passage so that intake air is accelerated moving distally through the delivery passage and delivery opening.

In additional embodiments, the exit opening is proximal of the delivery opening. In some such embodiments, the delivery opening is distal of the atomizer cup proximal edge. In further embodiments, a cross-sectional area of the vaporizing chamber increases along the vaporizing chamber flow path.

Yet additional embodiments comprise an exit groove formed in the side wall of the atomizer cup, the exit opening communicating with the exit groove, and the vapor flows distally through the exit groove.

Further embodiments, additionally comprise a distal vapor chamber distal of the atomizer cup, and a vapor tube extending proximally from the distal vapor chamber to a mouthpiece. In some such embodiments, a cross-sectional area of the delivery passage decreases moving distally along its length so that air flowing distally through the delivery passage is accelerated. In additional embodiments, delivery of accelerated air directed toward the distal wall of the atomizer cup imparts turbulent flow characteristics to the accelerated air.

In still further embodiments, the delivery opening directs a flow of air towards a center of the atomizer cup distal wall, and the exit opening is radially spaced from the center of the atomizer cup.

In yet further embodiments, the delivery opening directs a flow of air towards a first side of the atomizer cup, and the exit opening is at or adjacent a second side of the atomizer cup generally opposite the first side.

In yet additional embodiments, a cross-sectional area of the delivery opening is less than a cross-sectional area of the inlet passage so that intake air is accelerated moving distally through the delivery passage and delivery opening.

In still additional embodiments, a flow director extends distally beyond the distal end of the flow body and a tab extends distally from a distal wall of the flow director. In some such embodiments, the delivery passage is defined within the flow director, and the delivery opening is defined through the distal wall of the flow director. In further such embodiments, the tab is disposed adjacent the delivery opening. In still further such embodiments, a distal edge of the tab is disposed adjacent the heating element in the vaporizing chamber.

DESCRIPTION

Figure 1:
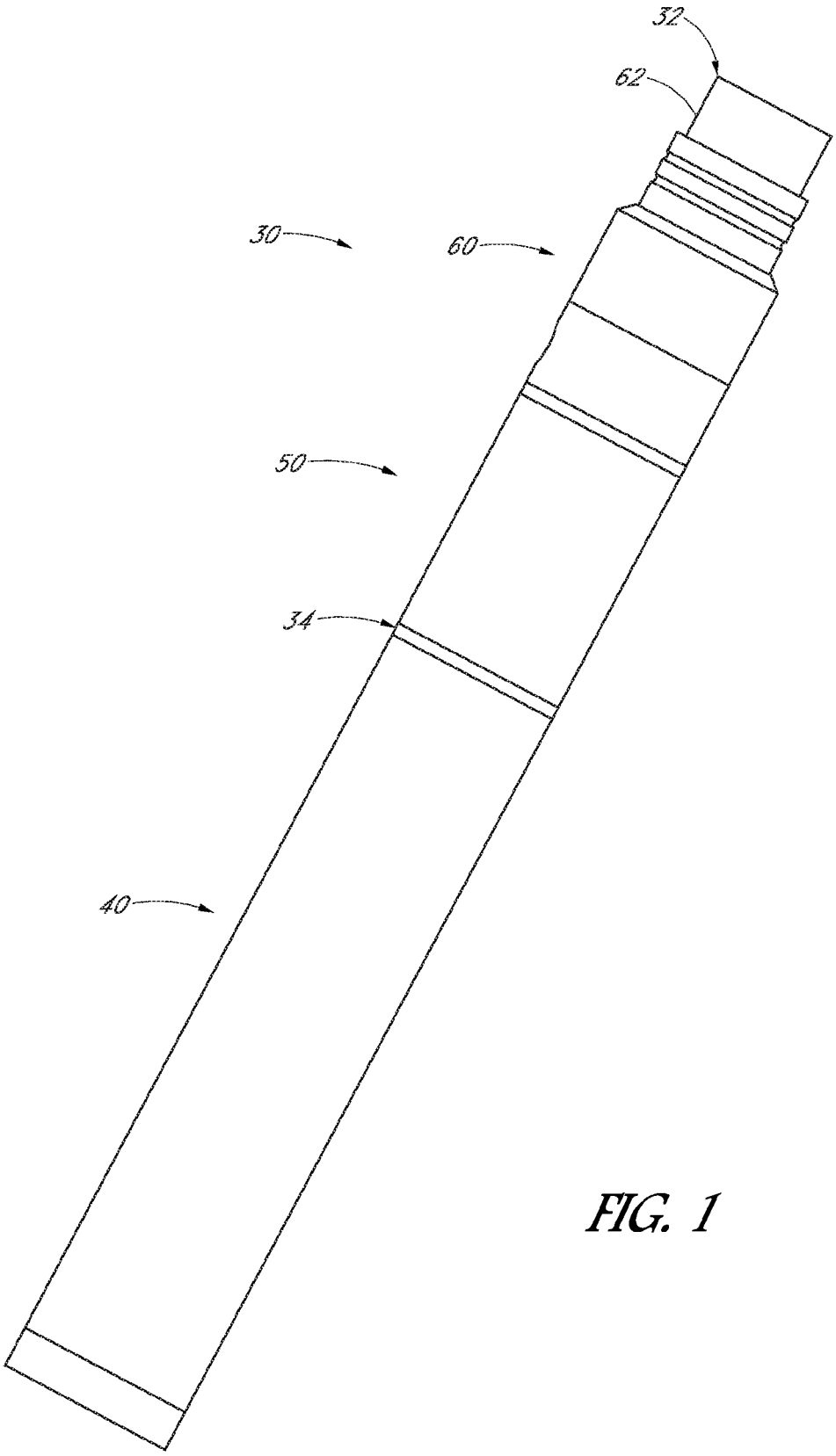
FIG. 1 is a perspective view of an embodiment of a personal vaporizer assembled with a battery.

With initial reference to FIGS. 1-6, one embodiment of a personal vaporizer 30 has a proximal end 32 and a distal end 34. A battery module 40 at the distal end includes a rechargeable battery enclosed within a battery casing, which battery module 40 preferably supplies electric power for the personal vaporizer. An atomizer module 50 is selectively attachable to the proximal end of the battery module and is configured to atomize the medium. Atomized medium is mixed with air, creating a vapor. An airflow module 60 is selectively attachable to the proximal end of the atomizer module 50. The airflow module [50] *60* preferably intakes ambient air for delivery to the atomizer module [60] *50*, and receives vapor from the atomizer module [60] *50*. A mouthpiece 62 is provided to direct vapor into a user's mouth.

Figure 2:
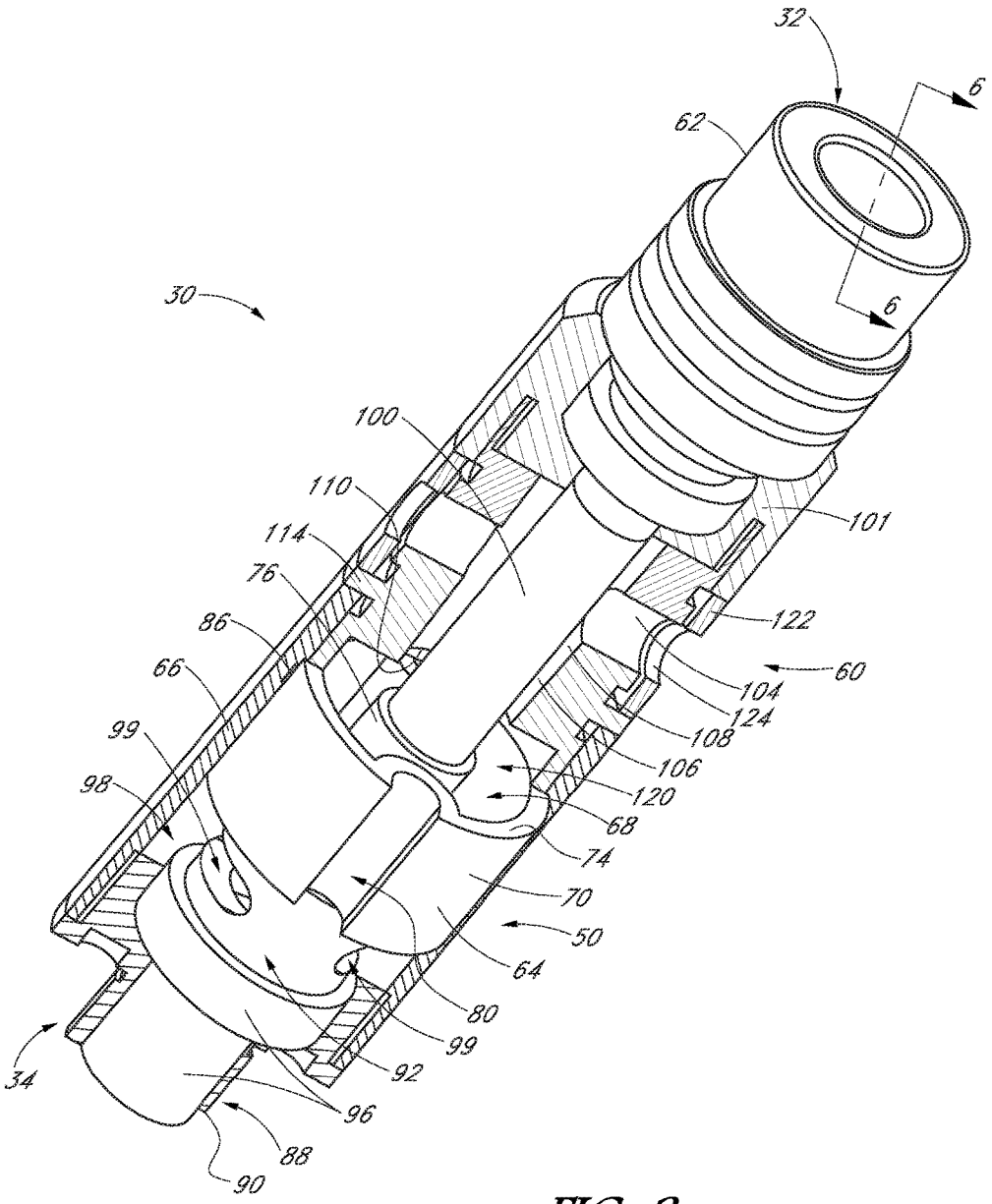
FIG. 2 is a partial cross-section view of the personal vaporizer of FIG. 1.
Figure 3A:
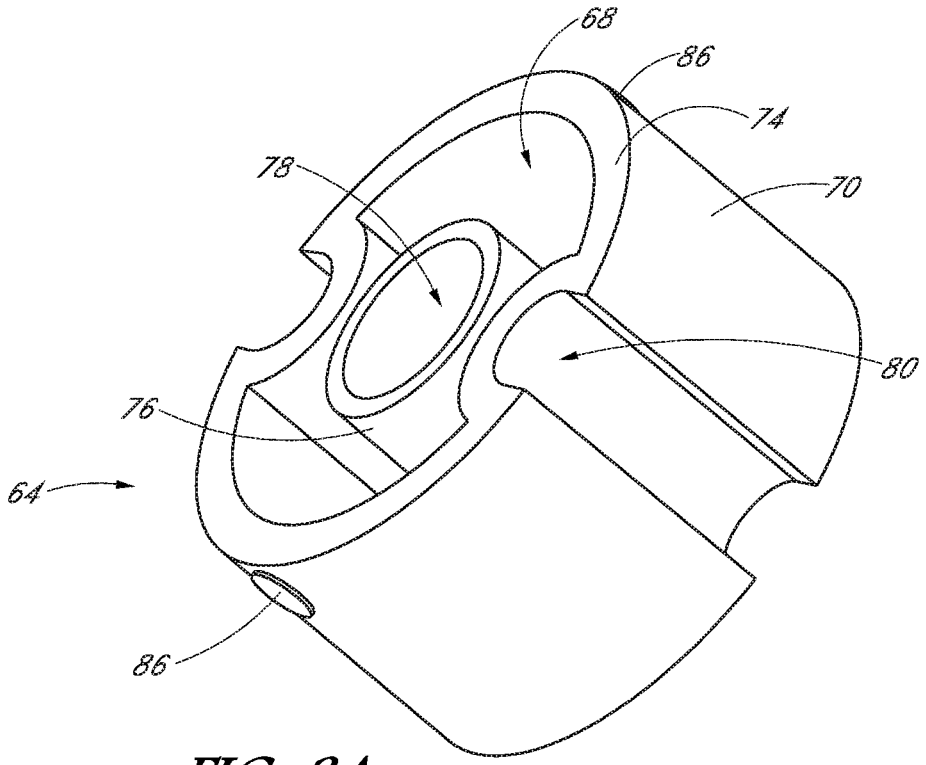
FIG. 3A is a perspective view of an atomizer cup of the personal vaporizer of FIG. 1.
Figure 3B:
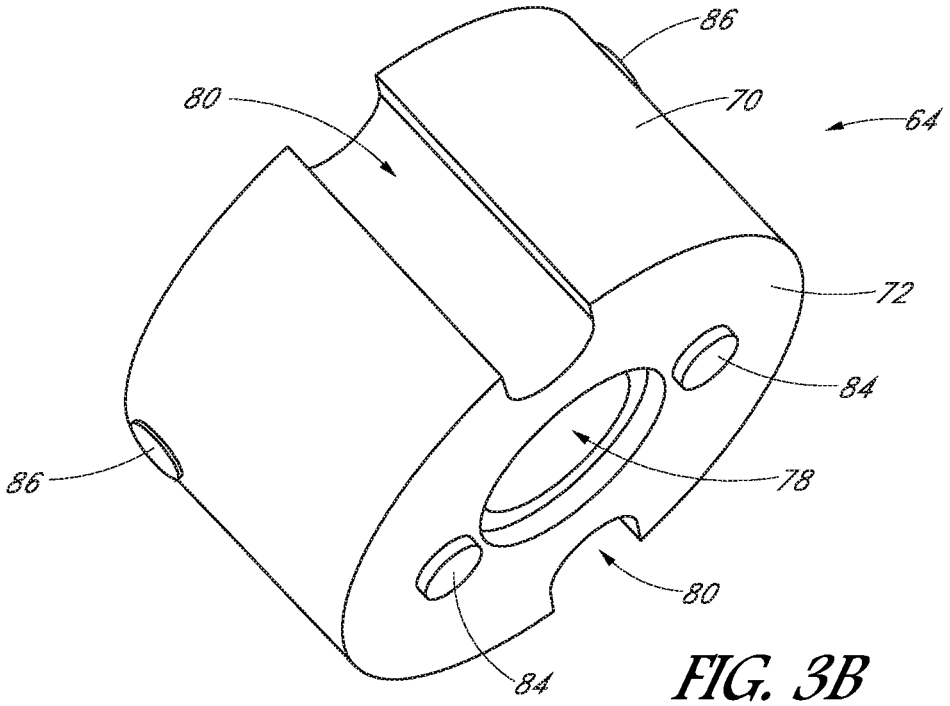
FIG. 3B is another perspective view of the atomizer cup of FIG. 3.
Figure 4:
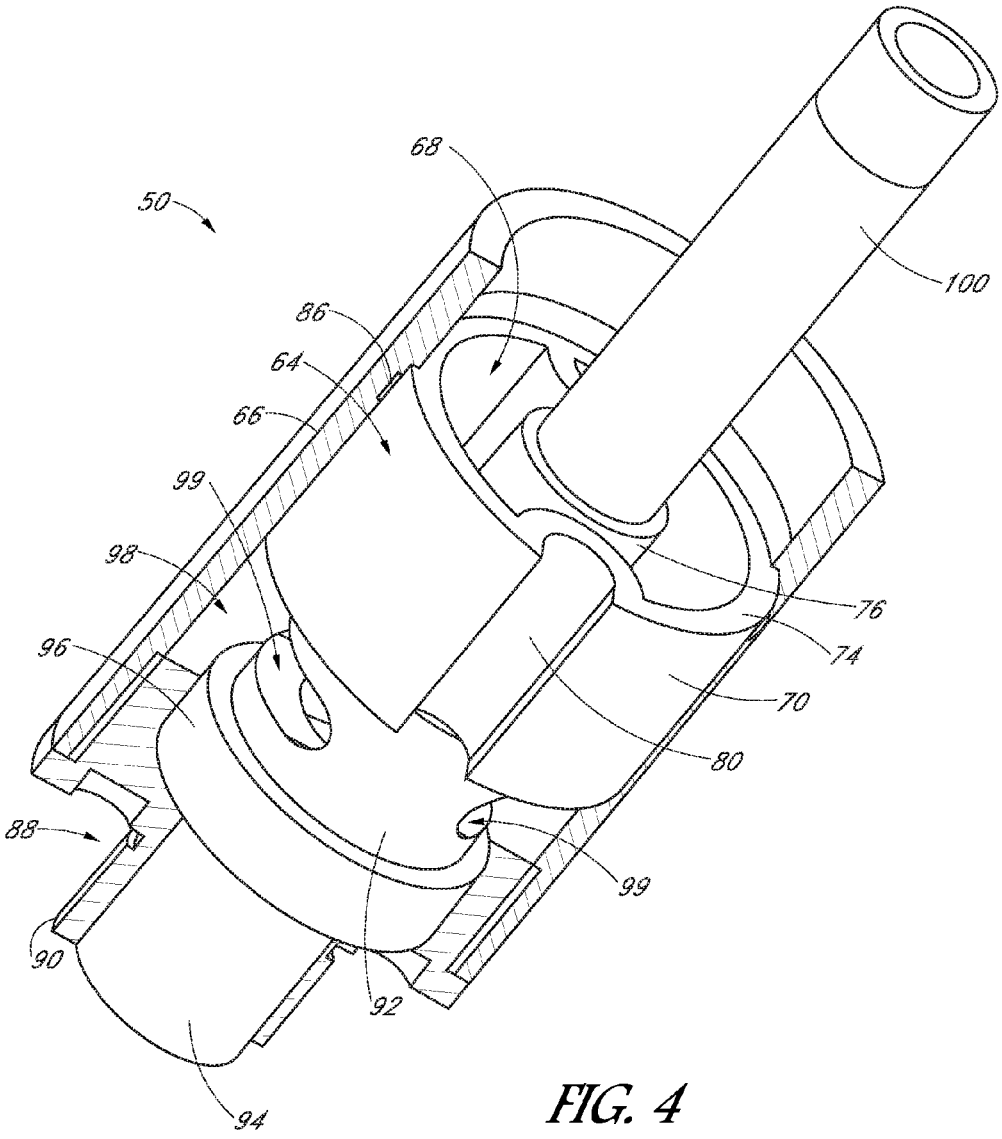
FIG. 4 is a partial cross-section view of an atomizer module of the personal vaporizer of FIG. 2.

With specific reference to FIGS. 2 and 3, the illustrated atomizer module 50 comprises an atomizer cup 64 held within an atomizer case 66. The atomizer cup 64 has a cup opening 68 that is configured to receive a vaporizing medium M such as a wax. With particular reference to FIGS. 2-4, the atomizer cup 64 includes a generally circumferential cup wall 70 and a bottom wall 72. The cup opening 68 is adjacent a top or proximal surface 74 of the cup wall 74 so as to define a space to hold vaporizing medium M, particularly a solid or semi-solid medium such as a wax. In the illustrated embodiment, the atomizer cup 64 includes a center wall 76 that defines a center aperture 78. As such, in the illustrated embodiment, medium M is held within the atomizer cup 64 in the space defined between the center wall 76, bottom wall 72 and cup wall 70.

In the illustrated embodiment, exit grooves 80 are formed in the cup wall 70 on opposite sides of the atomizer cup 64. The exit grooves 80 preferably are elongated and define a passage 82 from the top surface 74 of the atomizer cup 64 to and beyond the bottom wall 72. When the atomizer cup 64 is mounted within the atomizer case 66, an exit passage 82 is defined between the exit groove 80 and the adjacent atomizer case 66.

In the illustrated embodiment, the atomizer cup 64 includes a heating element (not shown). In a preferred embodiment, the atomizer cup 64 is formed of a ceramic material, and the heating element, such as a resistance wire, is encased within the ceramic. When the resistance wire is energized, it heats quickly, and correspondingly heats the ceramic cup, which in turn heats and atomizes the medium within the cup. In the illustrated embodiment, the atomizer cup includes two resistance wires encased therewithin. Each atomizer wire extends between a bottom wire interface 84 and a wall wire interface 86.

Energy is provided to the resistance wires by applying a voltage across one of the bottom wire interfaces 84 and its corresponding wall wire interface 86. More specifically, in the illustrated embodiment, the bottom wire interface 84 comprises an electrode communicating with the resistance wire that is encased within the atomizer cup, and the wall wire interface 86 includes an electrical node communicating with an opposite end of the resistance wire.

In the illustrated embodiment, the bottom and wall wire interfaces 84, 86 are illustrated as electrical nodes. In other embodiments, it should be appreciated that the interfaces may include wires extending from the atomizer cup 64. In still further embodiments, the atomizer cup may include a heating element that is not encased within the cup. For example, wire coils may be arranged within the cup between the cup wall, bottom surface and center wall.

Figure 6:
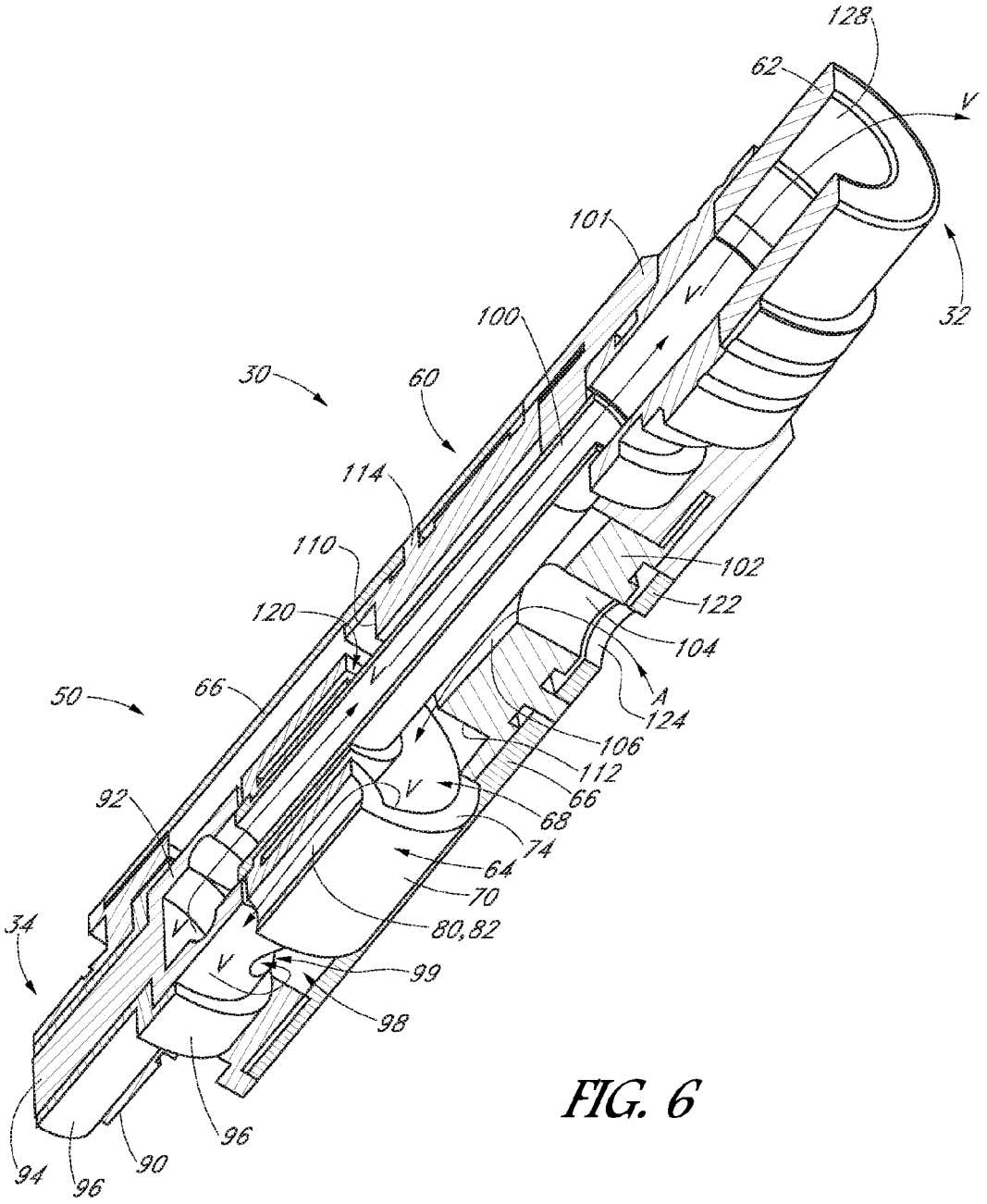
FIG. 6 is a perspective cross-sectional view of the personal vaporizer of FIG. 2 taken along line 6-6.

With continued reference to FIGS. 2-4 and additional reference to FIG. 6, the atomizer cup 64 preferably is mounted within the atomizer case 66 so as to engage the case. Most preferably, the wall wire interfaces 86 tightly engage the atomizer case 66, which preferably is constructed of an electrically conductive material. A connector pin 88 is provided at the distal end of the atomizer module 50 for physically and electrically connecting to the battery module 40. An outer pin portion 90 of the connector pin 88 is attached to and in electrical communication with the atomizer case 66. The outer pin portion 90 preferably is sized and shaped to engage a proximal connector of the battery module 40. For example, in some embodiments the outer pin portion 90 is threaded so as to be threadable onto such a battery module proximal connector. As such, the outer pin portion 90 is physically and electrically connected with an outer (second) node of the battery.

A connector 92 of the personal vaporizer 30 has a proximal end that engages the bottom wire interfaces 84 of the atomizer cup 64. The connector 92 preferably is electrically conductive, and extends distally so that an inner pin portion 94 of the connector 92 engages an inner (first) node of the battery module 40. An insulator sleeve 96 is disposed between the connector 92 and the outer pin portion 90 to electrically isolate the connector 92 from the outer pin portion 90. Preferably, when the vaporizer 30 is attached to the battery, the inner pin portion 94 engages the inner node of the battery while the outer pin portion 90 engages the outer node of the battery, which inner and outer nodes of the battery preferably have opposite polarity The proximal end of the connector 92 is engaged with the bottom wire interface 84. Thus, electric current is delivered to the heating element of the atomizer cup 64 from the battery 40 through the connector 92 and the bottom wire interfaces 84. After flowing through the heating element, electrical current flows through the wall wire interfaces 86 and into the atomizer case 66, from which it flows to the outer pin portion 90 and the second node of the battery module 40. As such, a circuit is provided to supply electrical energy from the battery module 40 to the heating element.

As shown, the connector 92 has a diameter less than that of the atomizer cup 64 so that a bottom chamber 98 is defined between an outer surface of the connector 92 and the inner surface of the atomizer case 66 below the bottom wall 72 of the atomizer cup 64. The exit passages 82 of the atomizer cup 64 communicate with this bottom chamber 98. One or more vapor openings 99 are defined in the connector 92, which is also aligned with a vapor tube 100. The vapor tube 100 communicates with the bottom chamber 98 through the connector vapor openings 98. The vapor tube 100 is an elongated tube that extends through the atomizer cup center aperture 78 and is supported by the atomizer cup center wall 76. A proximal end of the vapor tube 100 can be threaded so that it can be connected to a mouthpiece interface 101.

Figure 5:
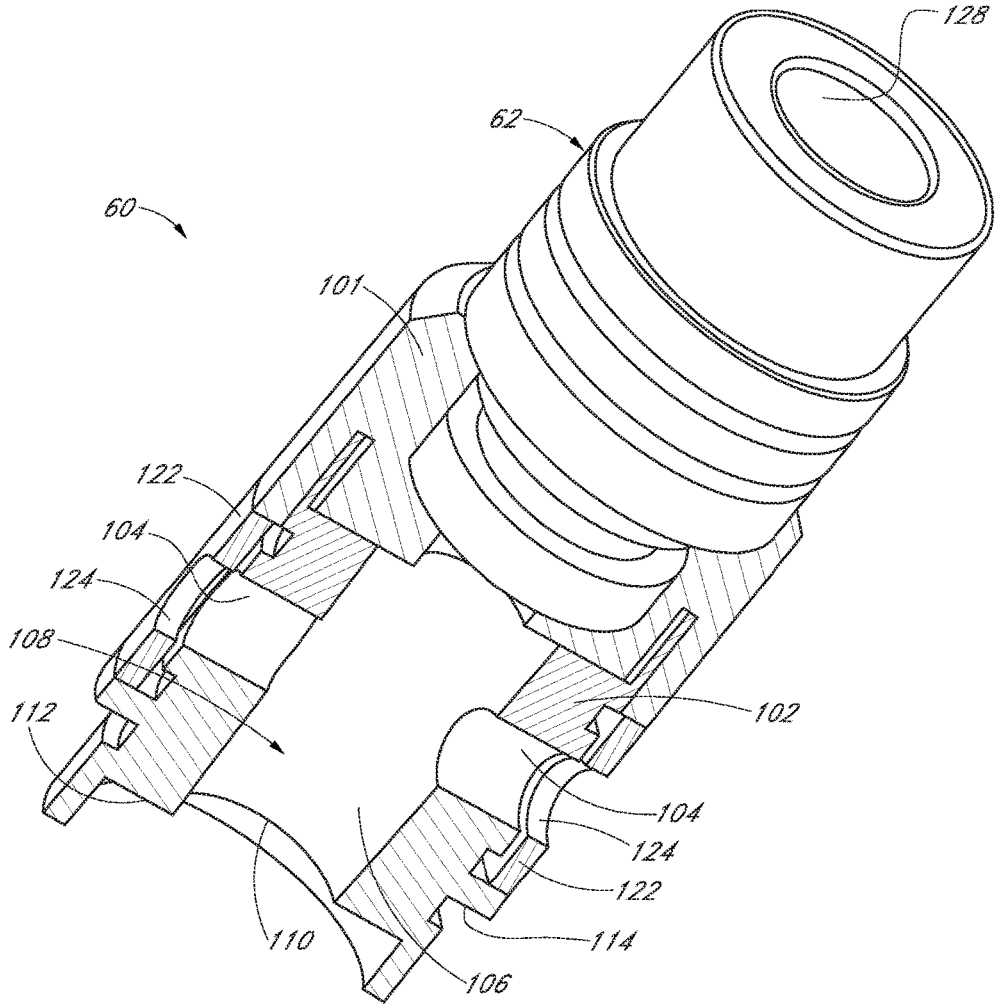
FIG. 5 is a partial cross-section view of an airflow module and mouthpiece of the personal vaporizer of FIG. 2.

With additional reference to FIG. 5, the airflow module 60 preferably is releasably connected to the atomizer module 50 such as by a threaded connection. As such, the user can remove the airflow module 60 so as to load vaporizing medium M into the atomizer cup 64. An airflow insert 102 includes a pair of inlet passages 104 that open to a side of the vaporizer. A delivery passage 106 is defined centrally within the airflow insert 102 and communicates with both inlet passages 104. As shown, the airflow insert 102 includes an elongated passage 108 that is sized and configured to accommodate the vapor tube 100 extending therethrough. The delivery passage 106 is defined between the vapor tube 100 and the walls of the elongated passage 108. In the illustrated embodiment, a downstream or distal opening 110 of the delivery passage 106 has a cross-sectional area that is less than the cross-sectional area of the delivery passage 106 at and adjacent the inlet passages 104. In a preferred embodiment, the distal opening 110 of the delivery passage 106 is sized and configured so that a total cross-sectional area of the delivery passage at the distal opening 110 is less than the combined cross-sectional area of the inlet passages 104. As such, airflow is accelerated moving distally through the delivery passage 106.

The distal opening 110 is formed through a distal wall 112 of the airflow insert 102. The distal wall 112 preferably extends generally transversely to an axis of the airflow module 60.

With continued reference to FIGS. 2 and 4-6, in the illustrated embodiment, the airflow insert 102 is threaded at its distal end so as to engage the proximal end of the atomizer casing 66. A stop 114 of the airflow insert 102 is configured to engage the proximal end of the atomizer case 66 so as to prevent the airflow insert 102 from being inserted too far distally into the atomizer case 66. As such, when connected, the distal wall 112 of the airflow insert 102 is positioned generally above, or proximal, the top or proximal edge 74 of the cup 64, and a vaporizing chamber 120 is defined between the atomizer cup 64 and the distal wall 112. It is to be understood, however, that in other embodiments the airflow insert 102 can be configured so that the distal wall 112 extends distally through the atomizer cup opening 68.

In the illustrated embodiment, the airflow insert 102 has a circumferential groove into which a throttle ring 122 is movably received. The throttle ring 122 includes two inlet apertures 124 that selectively align with the inlet passages 104. In some embodiments the throttle ring 122 can be rotated about the airflow insert 102 to vary the degree of alignment between the throttle ring inlet apertures 124 and the inlet passages 104. As such, rotation of the throttle ring 122 can selectively restrict flow into the inlet passages 104. In some embodiments, the throttle ring 122 can be ratcheted. In other embodiments there may be no throttle ring.

Continuing with reference to FIGS. 2, 5 and 6, an upper case or mouthpiece interface 101 can be attached to the proximal end of the airflow insert 102 such as by a removable threaded connection or, in other embodiments, a permanent connection such as adhesive or press-fitting. The mouthpiece interface 101 engages the proximal end of the vapor tube 100 and supports the mouthpiece 62. The mouthpiece 62 communicates the vapor tube 100 with an outlet 128 through which vapor V may flow.

With particular reference next to FIGS. 2 and 6, during operation, a user depresses a button (not shown) on the battery module 40 in order to activate the heating element, which thus heats a vaporizing medium M such as a wax disposed within the atomizer cup 64. Preferably, the medium is heated sufficiently that it atomizes. The user also engages the mouthpiece and sucks so as to establish a vacuum at the outlet 128. Ambient air A from outside the personal vaporizer 30 is drawn through the throttle inlets 124 into the inlet passages 104 and further into the delivery passage 106. Air within the delivery passage 106 is directed distally through the cup opening 68 and into the cup 64. Since the cross-sectional area of the delivery passage 106 decreases moving distally, the intake air A is accelerated as it flows through the delivery passage 106. The accelerated air A is directed into the vaporizing chamber 120, where it contacts and/or is mixed with medium M that is being heated and atomized by the heating element. The atomized medium M mixes with and becomes entrained into the air A, creating a vapor V.

As shown in the illustrated embodiment, accelerated ambient air A is directed by the delivery passage 106 in a distal direction into the atomizer cup 64 at or adjacent the center wall 76 of the atomizer cup 64. As the accelerated air A contacts the cup 64 and/or vaporizing medium M, the flow becomes at least partially turbulent. Also, the vacuum created by the user sucking on the mouthpiece 62 draws air to and through the exit grooves 80. However, air flow within the vaporizing chamber 120 is comparatively slowed after exiting the delivery passage 106. Further, the air flow path extends from the center wall 76 radially outwardly and also proximally over the top or proximal surface 74 of the atomizer cup 64 to get to the exit grooves 80. Thus, the air flow path includes dramatic direction changes within the vaporizing chamber 120 and follows a fairly long flow path through the vaporizing chamber. In the illustrated embodiment, the air flow changes direction about 90° or more once it exits the delivery passage 106, and changes direction another about 90° to extend proximally to the exit grooves 80. Thus, the air flow path changes direction about 180° within the vaporizing chamber 120. Factors such as the turbulent flow, slowing of the flow 180° direction changes, and a relatively long flow path each contribute to extending the period in which air A is in contact with the atomized vaporizing medium M within the vaporizing chamber 120. Such extended contact results in greater entrainment of atomized medium with the air, thus creating a more concentrated higher quality vapor V than in prior art personal vaporizers.

The vapor V is drawn proximally within the vaporizing chamber 120 and over the proximal surface 74 of the cup 64 to the exit grooves 80, through which it is drawn distally and past the atomizer cup 64 into the bottom chamber 98 defined distal of the atomizer cup 64. Vapor V within the bottom chamber 98 flows through the vapor openings 99 of the connector 92 and is drawn into the vapor tube 100, through which it flows proximally to the mouthpiece 62 and out of the mouthpiece outlet 128.

Figure 7:
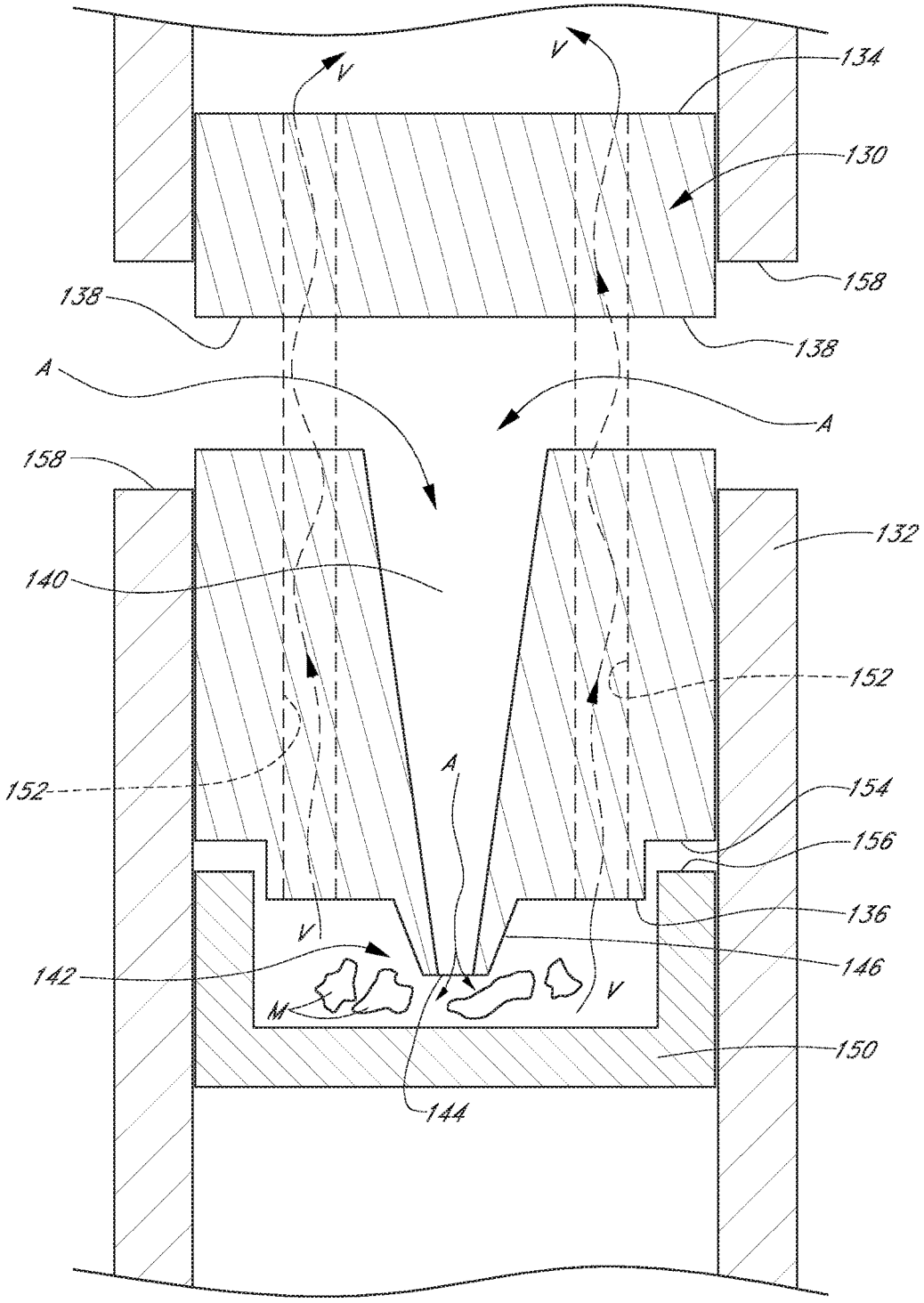
FIG. 7 is a partial sectional view of a personal vaporizer configured in accordance with another embodiment.

With reference next to FIG. 7, another embodiment is illustrated schematically. In this embodiment, an airflow insert 130 is threadingly engaged with a casing 132. The airflow insert 130 is generally elongated, extending from a proximal wall 134 to a distal wall 136. Inlet passages 138 open through a side of the airflow insert 130 and communicate ambient air A to a delivery passage 140, which is positioned generally centrally, or axially, within the airflow insert 130. As shown, the delivery passage 140 is tapered so as to accelerate air flowing distally therethrough, and terminates at a distal opening 144 defined at a delivery tip 146. A vaporization chamber 142 is defined between an atomizer cup 150 and the distal wall 136 of the airflow insert 130. A vaporizing medium M, such as a wax, can be disposed within the atomizer cup 150 and vaporized by a heating element of the atomizer cup 150.

Continuing with reference to FIG. 7, in the illustrated embodiment, the delivery tip 146 extends distally from the distal wall 136 of the airflow insert 130. Thus, the distal opening 144 of the delivery passage 140 is distal of the distal wall 136. As shown, intake air A that is accelerated into the vaporization chamber 142 flows into and through wax M that is being atomized, so that the atomized wax becomes entrained therein, forming a vapor V. Preferably, exit passages 152 are formed through the airflow insert 130, and the vapor V from the vaporization chamber 142 can flow proximally through the exit passages 152, preferably eventually being directed to a mouthpiece and outlet (not shown). Preferably, exit passage openings 153 are formed through the distal wall of the airflow insert 130 and positioned so that intake air must flow radially outwardly within the vaporization chamber 142 from its injection point to its exit point, increasing the entrainment of atomized wax into the air and improving vapor quality. Additionally, and as shown, the air injection point (the distal opening 144 the delivery passage 140) in the illustrated embodiment is distal of the exit passage openings 153. Further, as shown, the flowpath includes a redirection by 180° within the vaporization chamber 144.

In the illustrated embodiment, the position of the airflow insert 130 relative to the cup 150 can be adjusted such as by threadingly rotating the insert 130 within the casing 132. For example, the airflow insert 130 can be threadingly advanced further distally or proximally within the casing 132 from its position as shown in FIG. 7. If threaded further distally, it can be advanced distally until a stop surface 154 of the insert 130 engages the top or proximal surface 154 of the atomizer cup 150. In such a position, the distal opening 144 of the delivery passage 140 would be disposed well below the uppermost part of the wax medium disposed within the atomizer cup 150. As such, accelerated intake air A is injected directly into the wax M that is being atomized. Further, when moving the airflow insert 130 distally, the distal wall 136 of the insert 130 is positioned quite close to the atomizer cup 150, effectively creating a relatively small vaporizing chamber 142, which can also affect vapor quality. This enables a user to customize the volume of the vaporizing chamber 142 and the position of ambient air injection within the vaporizing chamber 142 by adjusting the position of the airflow insert 130 relative to the casing 132.

In the illustrated embodiment, inlet openings 158 are formed through the casing 132 so as to align with the inlet passages 138 of the airflow insert 130. Preferably, however, the diameter of the inlet openings 158, or at least the distance between the proximal-most and distal-most edges of the inlet openings 158, is greater than a diameter of the inlet passages 138 so that the inlet passages 138 remain unobstructed by the casing 132 over a range of advancement of the airflow insert 130 relative to the casing 132.

Figure 8:
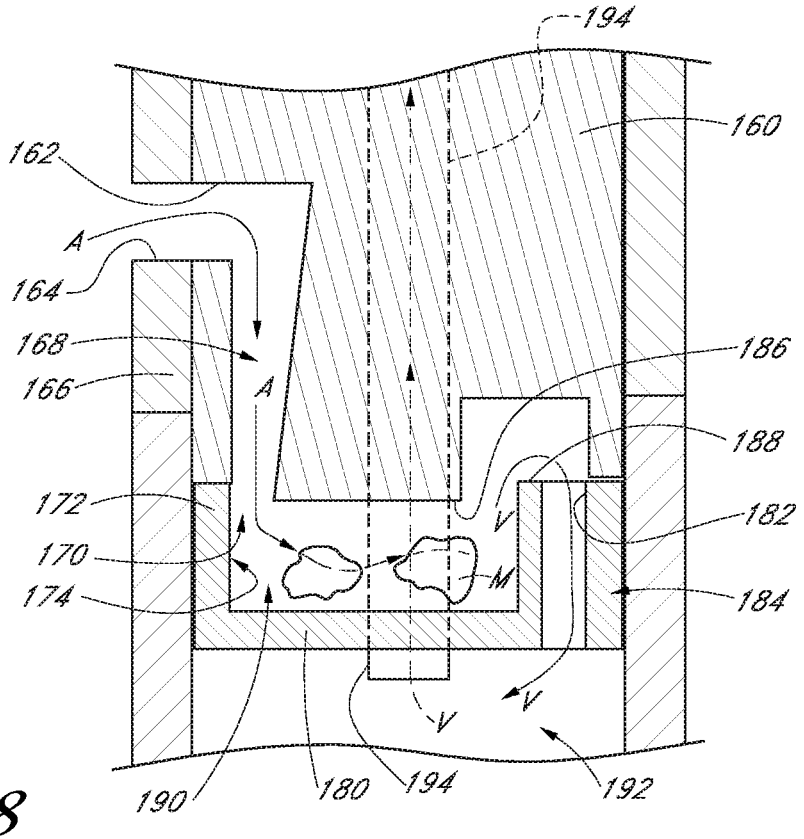
FIG. 8 is a partial sectional view of a personal vaporizer configured in accordance with yet another embodiment.

With reference next to FIG. 8, yet another embodiment is depicted schematically. In this embodiment, an airflow insert 160 has a side opening 162 aligned with an inlet aperture 164 of a casing 166. The side opening 162 leads to a tapered delivery passage 168 having a distal opening 170 generally aligned with a side wall 172 at a first side 174 of an atomizer cup 180. An exit groove or passage 182 is defined through the atomizer cup 180 at a second side 184 of the cup 180 opposite the delivery passage opening 170. In the illustrated embodiment, a distal wall 186 of the airflow insert 160 is distal of the top, or proximal, edge 188 of the atomizer cup 180. A vaporizing chamber 190 is defined between a cup 180 and the distal wall 186 of the insert 160.

Continuing with reference to FIG. 8, ambient air A is drawn through the side opening 162 and accelerated distally through the delivery passage 168 into the atomizer cup 180 at the first side 174 of the vaporizing chamber 190. As the accelerated air A contacts the atomizer cup 180 and/or vaporizing medium M, it is redirected and becomes at least partially turbulent. Also, air flow substantially slows within the vaporizing chamber 190, which has a cross-sectional area much greater than the delivery passage 168 distal opening 170. Due to the vacuum from the user sucking on the mouthpiece, the air is drawn from the first side 174 of the vaporizing chamber 190 to the exit groove 182 at the second side 184. As it flows through the vaporizing chamber 190 the air A flows through an atomized wax medium M, which becomes entrained in the air so as to form a high-quality vapor V. The vapor V flows proximally over the top edge 188 of the cup 180 and then distally through the exit groove 182 to a bottom vapor chamber 192 distal of the atomizer cup 180. The vapor then enters a vapor tube 194 which directs it proximally toward an outlet.

Figure 9:
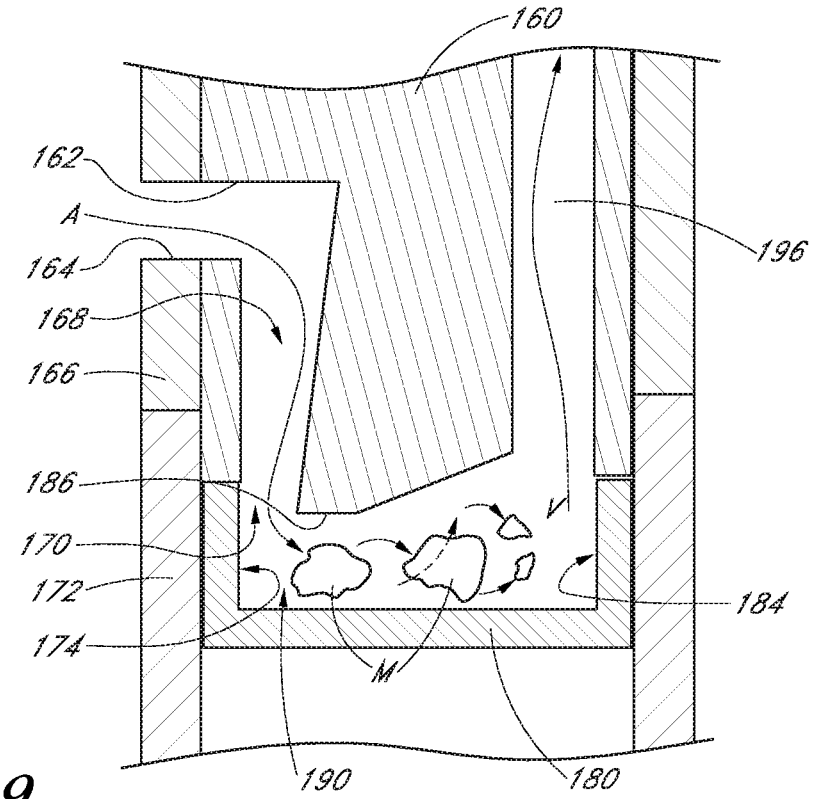
FIG. 9 is a partial sectional view of a personal vaporizer configured in accordance with a further embodiment.
Figure 10:
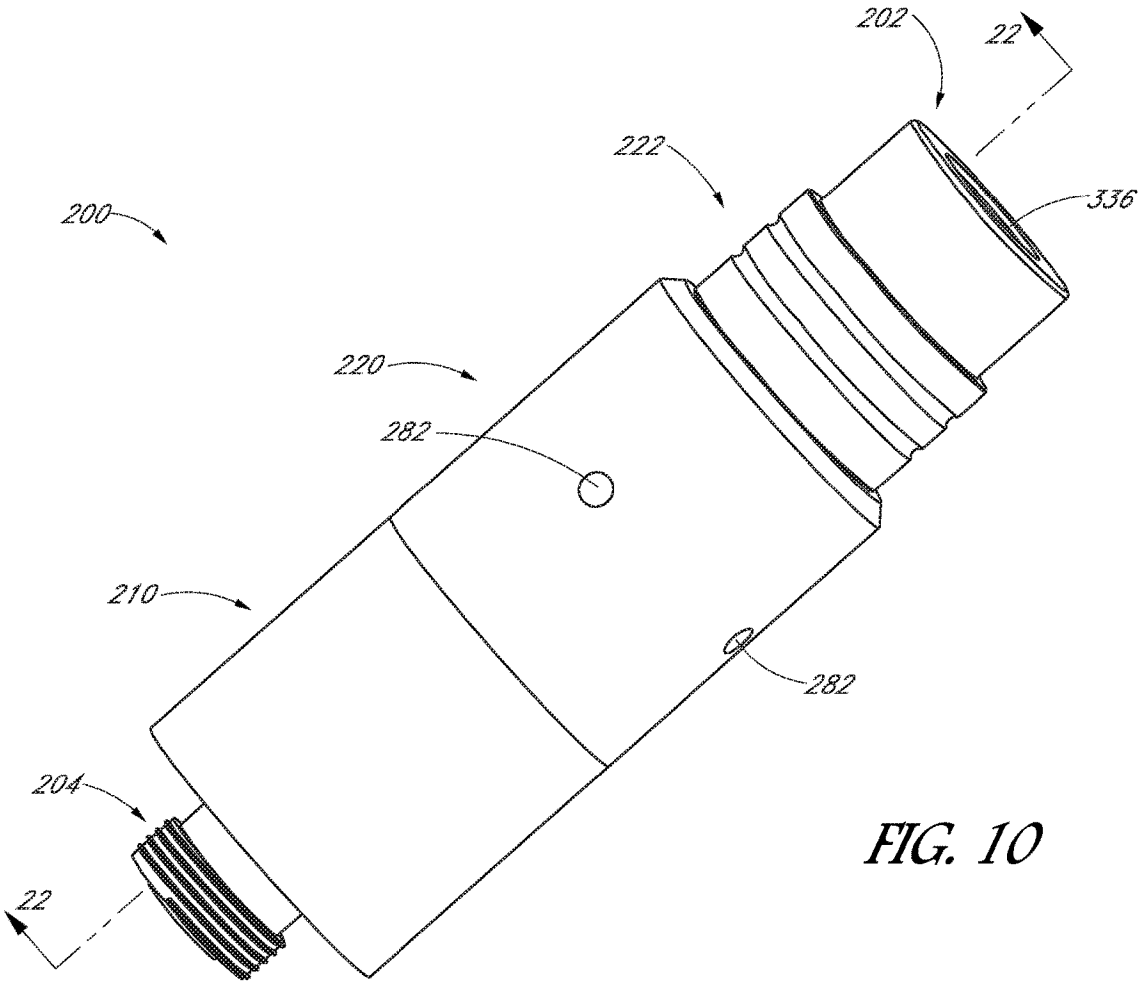
FIG. 10 is a perspective view of still another embodiment of a personal vaporizer.

With reference next to FIG. 9, a still further embodiment is depicted schematically, which embodiment shares some similar structure with other embodiments. In this embodiment, an airflow insert 160 has a side opening 162 aligned with an inlet aperture 164 of a casing 166. The side opening 162 leads to a tapered delivery passage 168 having a distal opening 170 generally aligned with a side wall 172 at a first side 174 of an atomizer cup 180. An exit passage 196 is defined within the insert 160 and arranged at or adjacent a second side 184 of the cup 180 opposite the delivery passage opening 170. In the illustrated embodiment, a distal wall 186 of the airflow insert 160 is distal of the top, or proximal, edge 188 of the atomizer cup 180 adjacent the first side 174, but the distal wall 186 is tapered moving towards the second side 184. A vaporizing chamber 190 is defined between the cup 180 and the distal wall 186 of the insert 160. Due to the tapered distal wall 186, the cross-sectional area of the vaporizing chamber 190 increases moving from the first side 174 to the second side 184.

Continuing with reference to FIG. 9, ambient air A is drawn through the side opening 162 and accelerated distally through the delivery passage 168 into the atomizer cup 180 at the first side 174 of the vaporizing chamber 190. As the accelerated air A contacts the atomizer cup 180 and/or vaporizing medium M, it is redirected and becomes at least partially turbulent. Also, air flow substantially slows within the vaporizing chamber 190, which has a cross-sectional area much greater than the delivery passage 168 distal opening 170. Due to the vacuum from the user sucking on the mouthpiece, the air is drawn from the first side 174 of the vaporizing chamber 190 to the exit groove 182 at the second side 184. As it flows through the vaporizing chamber 190 the air A flows through an atomized wax medium M, which becomes entrained in the air so as to form a high-quality vapor V. Since the cross-sectional area of the vaporizing chamber 190 increases moving from the first side 174 to the second side 184, airflow is further slowed, leading to even better entrainment of medium M into the air A. After passing through the vaporizing chamber 190, the vapor V is drawn proximally through the exit passage 196 toward an outlet.

With reference next to FIGS. 10-22, another embodiment of a personal vaporizer 200 has a proximal end 202, a distal end 204, an atomizer module 210, a flow module 220, and a mouthpiece module 222. The atomizer module 210 is selectively attachable to a battery and is configured to atomize the vaporizing medium. Atomized medium is mixed with air, creating vapor, in the atomizer module 210. The flow module 220 is selectively attachable to the proximal end of the atomizer module 210. The flow module 220 intakes ambient air, delivers air to the atomizer module 210, receives vapor from the atomizer module, and communicates the vapor to the mouthpiece module 222. The mouthpiece module 222 attaches to the proximal end of the flow module 220 and is configured to receive vapor from the flow module and direct the vapor into a user's mouth. In some embodiments, all or part of the mouthpiece module may be incorporated into the flow module.

With specific reference to FIGS. 11-15, the illustrated atomizer module 210 comprises an atomizer cup 230 that fits within an atomizer casing 232. A connector pin 234 and an insulating sleeve 236 also fit within the casing 232 distal of the cup 230, and a heating element 240 fits within the atomizer cup 230. In the illustrated embodiment, a spacing ring 242 fits within the casing 232 proximal of the cup 230.

The atomizer cup 230 includes a transverse wall 244 and a circumferential side wall 246 having a top or proximal edge 248 and a bottom or distal edge 250. A cup opening 252 is defined adjacent the proximal edge 248 of the cup side wall 246. The atomizer cup 230 is configured to receive a vaporizing medium M such as a wax. First and second apertures 254, 256 are formed through the transverse wall 244. A heating element seat 258 is formed in the proximal side of the transverse wall 244. Similarly, a distal recess 260 is formed on the distal side of the transverse wall 244. As such, the circumferential distal edge 250 of the side wall 246 encircles the distal recess 260 of the transverse wall 244. A groove 262 is formed through the side wall 246 and is aligned with the first aperture 254.

Figure 13:
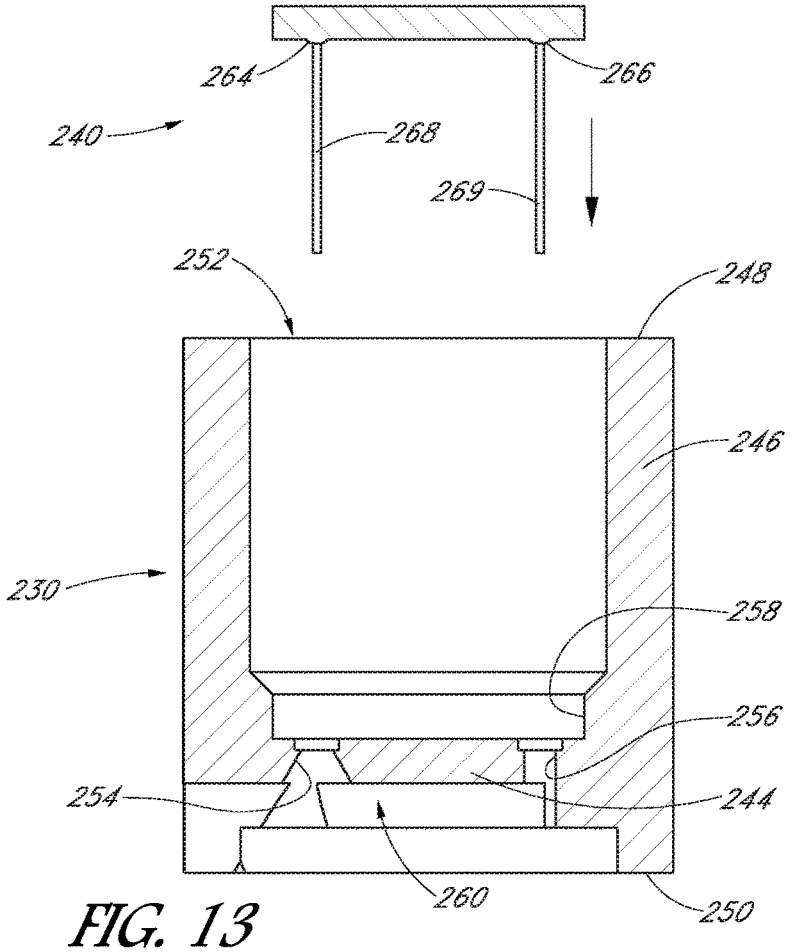
FIG. 13 is a cross-sectional view of the atomizer cup of FIG. 12A taken along line 13-13, and additionally showing a heating element.
Figure 14:
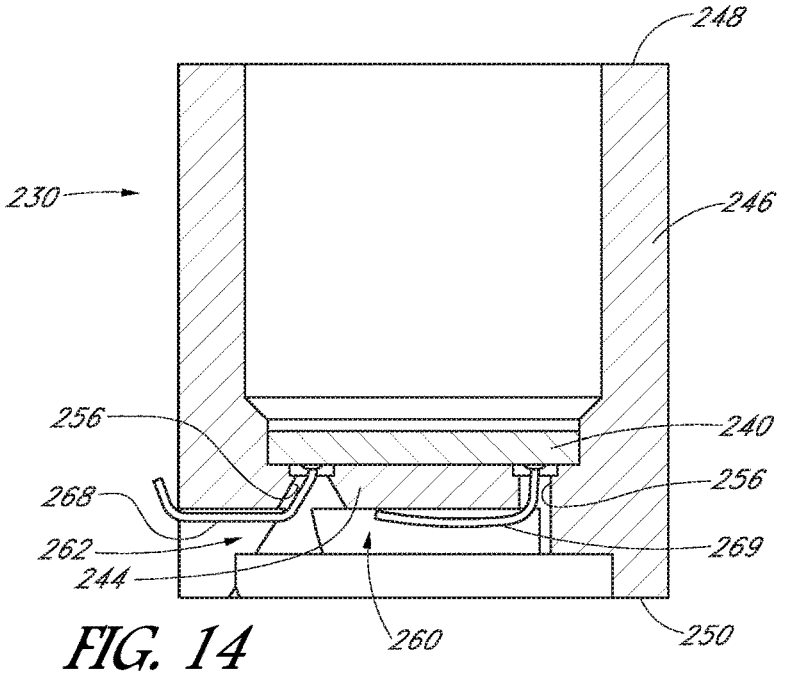
FIG. 14 shows the atomizer cup of FIG. 13 with the heating element installed.

With particular reference to FIGS. 13 and 14, the illustrated heating element 240 comprises a ceramic disc with a resistance wire encased therewithin. First and second nodes 264, 266 extend from the ceramic disc in order to allow electrical contact with opposing ends of the encased wire. Preferably a first wire 268 is soldered or otherwise attached to the first node 264, and a second wire 269 is soldered or otherwise attached to the second node 266. As best shown in FIGS. 13 and 14, during manufacture, the heating element 240 is advanced through the cup opening 252 and placed in the heating element seat 258. The first and second wires 268, 269 extend through the first and second apertures 254, 256, respectively. The first wire 268 preferably is then formed to fit through and within the groove 262 so that it extends radially outwardly of the side wall 246. The second wire 269 preferably is bent radially inwardly to fit adjacent the transverse wall 244.

Figure 11:
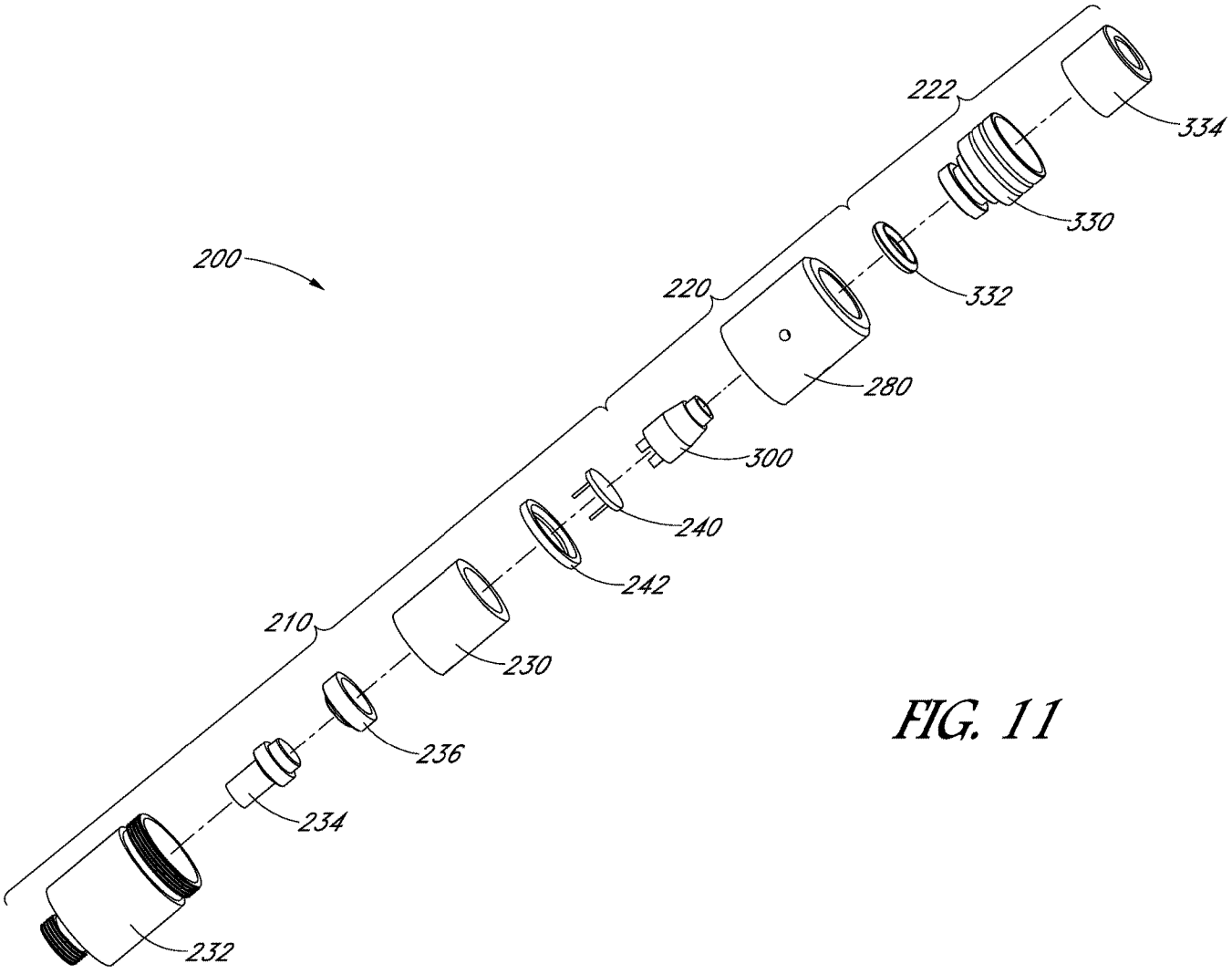
FIG. 11 is an exploded view of the personal vaporizer of FIG. 10.
Figure 12A:
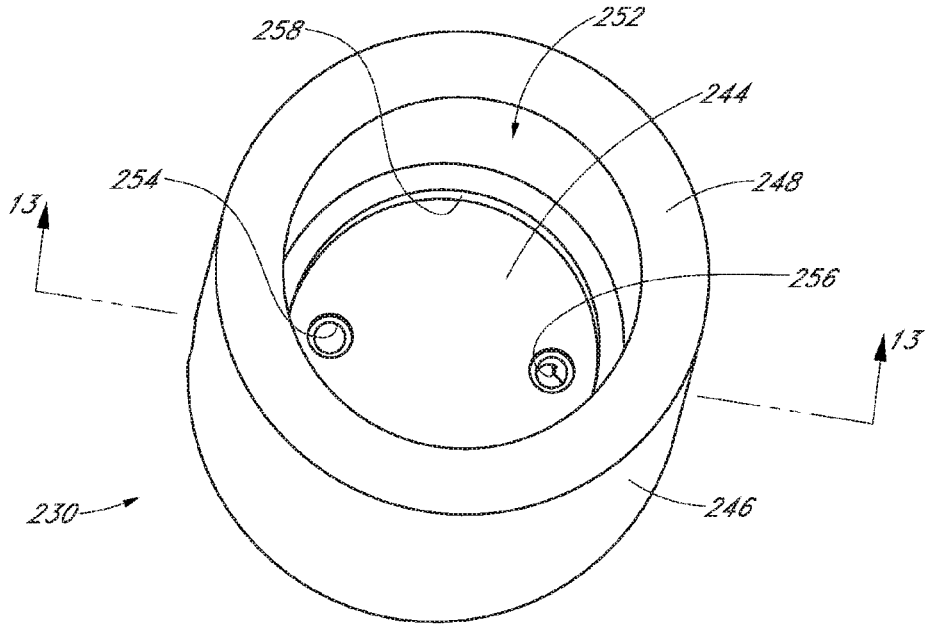
FIG. 12A is a perspective view of an atomizer cup of the personal vaporizer of FIG. 10.
Figure 12B:
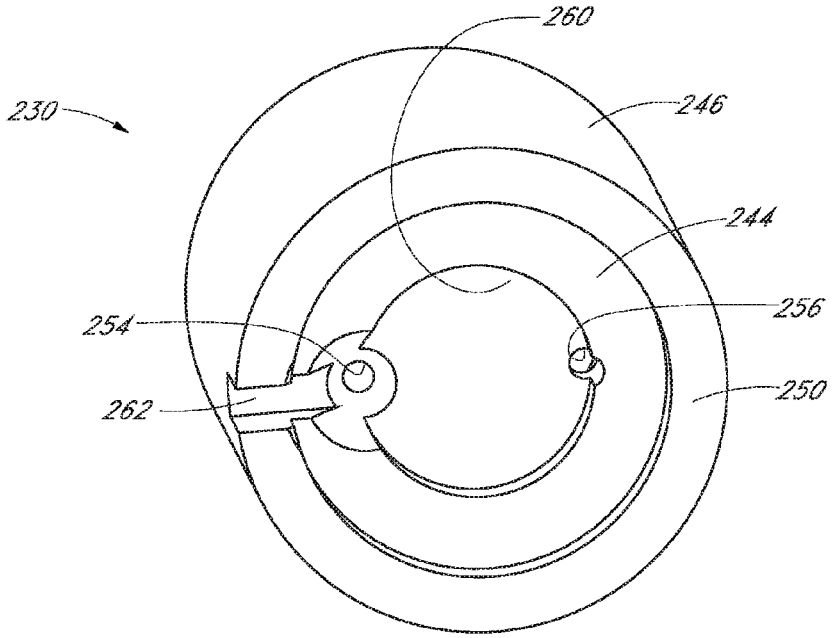
FIG. 12B is another perspective view of the atomizer cup of the personal vaporizer of FIG. 10.
Figure 15:
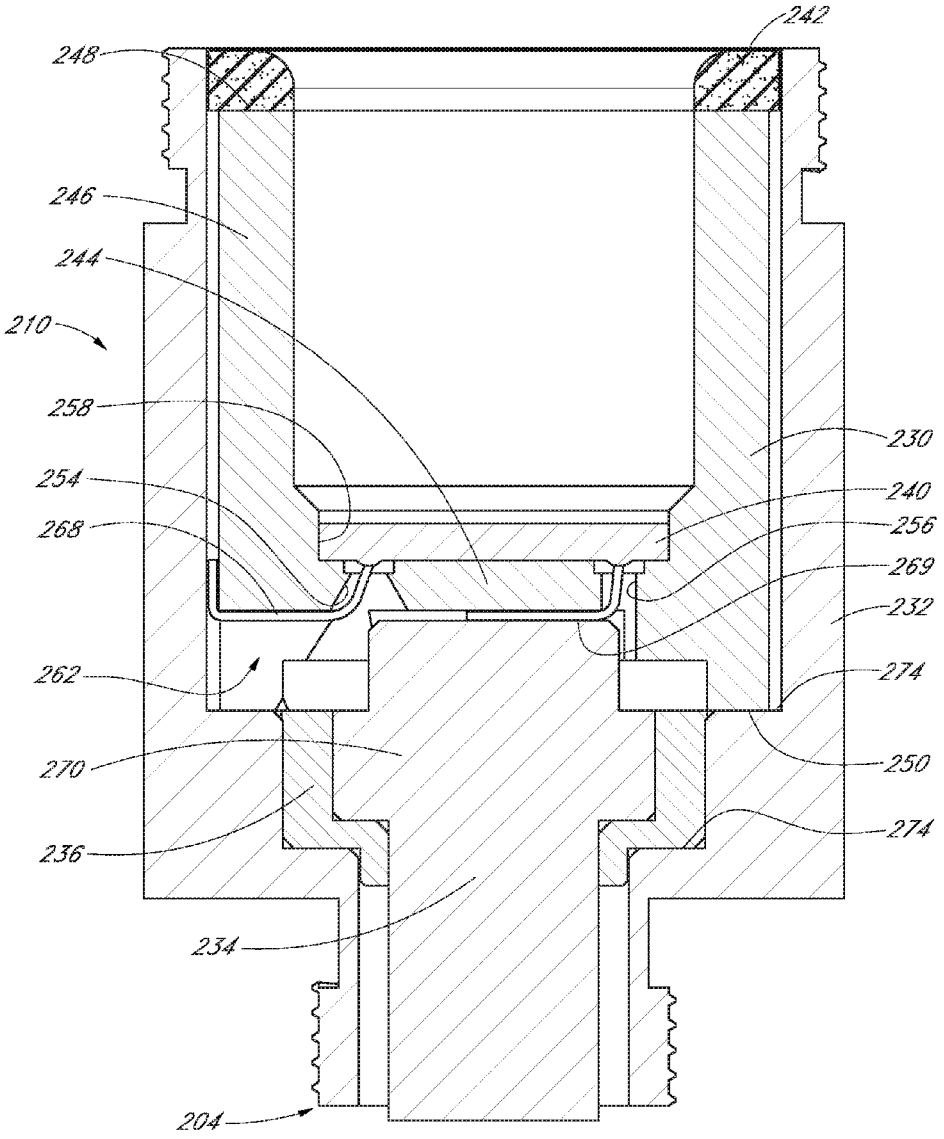
FIG. 15 is a sectional view of an atomizer module of the personal vaporizer of FIG. 10.
Figure 16:
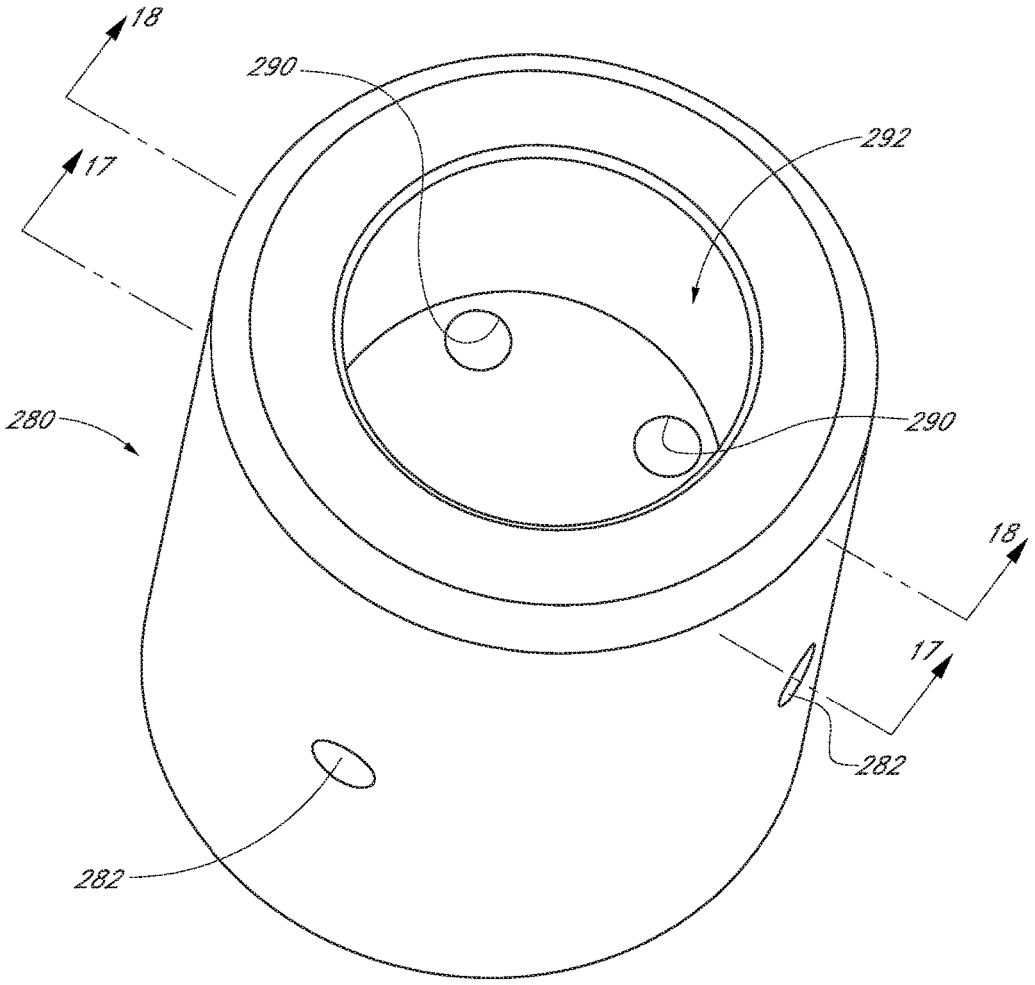
FIG. 16 is a perspective view of a flow director of the personal vaporizer of FIG. 10.
Figure 17:
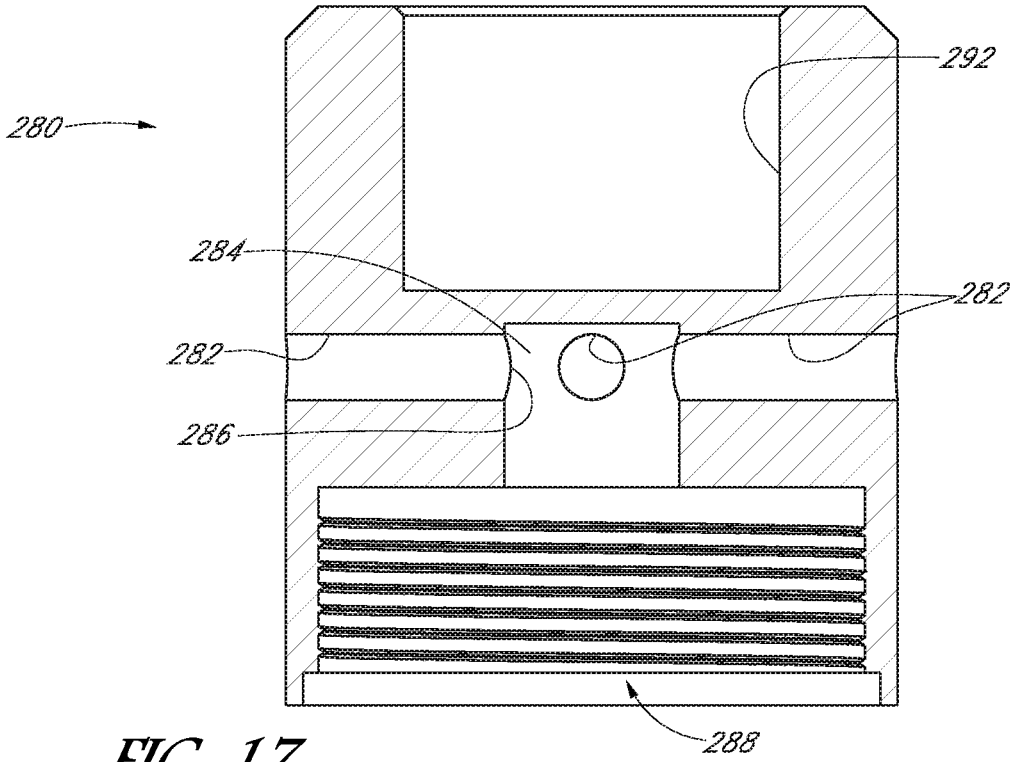
FIG. 17 is a cross-sectional view of the flow director of FIG. 16 taken along lines 17-17.
Figure 18:
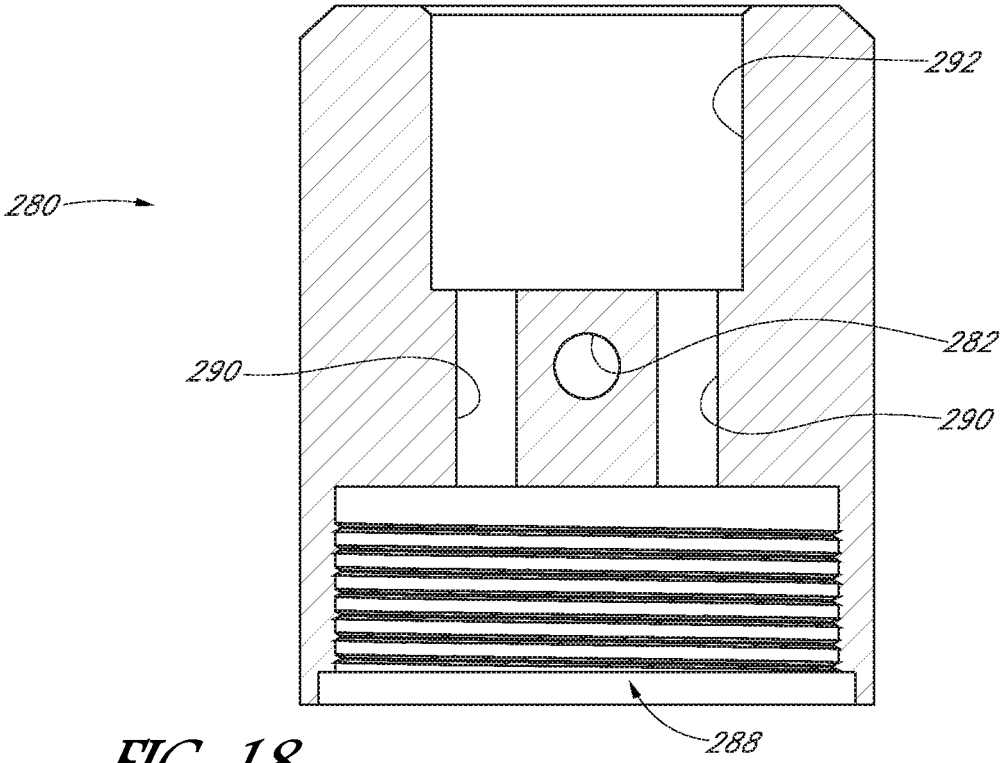
FIG. 18 is a cross-sectional view of the flow director of FIG. 16 taken along lines 18-18.

With particular reference to FIGS. 11 and 15, in the illustrated embodiment, the connector pin 234 preferably is elongated and formed of an electrically conductive material such as a metal. A ring portion 270 of the connector pin 234 has an increased diameter relative to other portions of the connector 234. The insulating sleeve 236 preferably is electrically nonconductive and is shaped complementarily to the connector 234 and its ring portion 270. During manufacture, preferably the insulating sleeve 236 is engaged with the connector pin 234, and the connector and sleeve are advanced into the atomizer casing 232 so that the sleeve and connector are received into a connector seat 272 defined within the casing 232. As shown, the connector pin 234 is either spaced from the casing 232 or electrically insulated therefrom by the insulating sleeve 236. In the illustrated embodiment, the connector pin 234 extends distally of the distal end 202 of the casing/personal vaporizer 200. Preferably, the distal end 202 is configured to attach to a mount boss of a typical battery so that the connector pin 234 and casing 232 engage battery nodes having opposing polarity.

Once the connector pin 234 is in place, the assembled atomizer cup 230 and heating element 240 are advanced into the casing 232 so that the distal edge 250 of the cup side wall 246 engages a step 274 on the casing 232. At this position, the atomizer cup 230 is adjacent the connector pin 234 so that the second wire 269 is sandwiched between the connector pin 234 and the transverse wall, but the first wire 268 is sandwiched between the atomizer cup side wall 246 and the casing 232 and is not in contact with the connector pin 234. As such, the second wire 269 is electrically connected to the connector pin 234, but the first wire 268 is electrically connected to the casing 232 which, in the illustrated embodiment, is formed of an electrically conductive material. In this arrangement, a current flow path is defined from the battery through the connector pin 234 and second wire 269 to the heating element 240, where it energizes the resistance wire to create heat. Electric current continues from the heating element 240 to the first wire 268 and further to the casing 232, from which the current returns to the battery.

Continuing with reference to FIG. 15, the spacer ring 242 preferably is placed atop the atomizer cup 230 within the casing 232. In some embodiments, the spacer ring 242 is press fit or otherwise arranged within the casing, and helps maintain the position of the cup and other components within the casing. Other embodiments may not employ such a spacer ring.

With reference next to FIGS. 10, 11, and 16-18, the flow module 220 comprises an elongated flow body 280 having a plurality of inlet passages 282 that open through a side of the flow body 280 and lead to an inlet center space 284 defined within the flow body 280 and along an axis of the vaporizer 200. The inlet center space 284 includes a receiver portion 286. A distal end of the flow body 280 defines an internally threaded opening 288 that is configured to engage the proximal threads of the atomizer casing 232. A plurality of exit passages 290 are also formed within the flow body 280. The exit passages 290 are radially spaced from the axis, but extend in a generally axial direction and do not intersect the inlet passages 282. As such, the exit passages 290 communicate the opening 288 with a proximal mouthpiece receiver 292 formed within the flow body 290.

Figure 19:
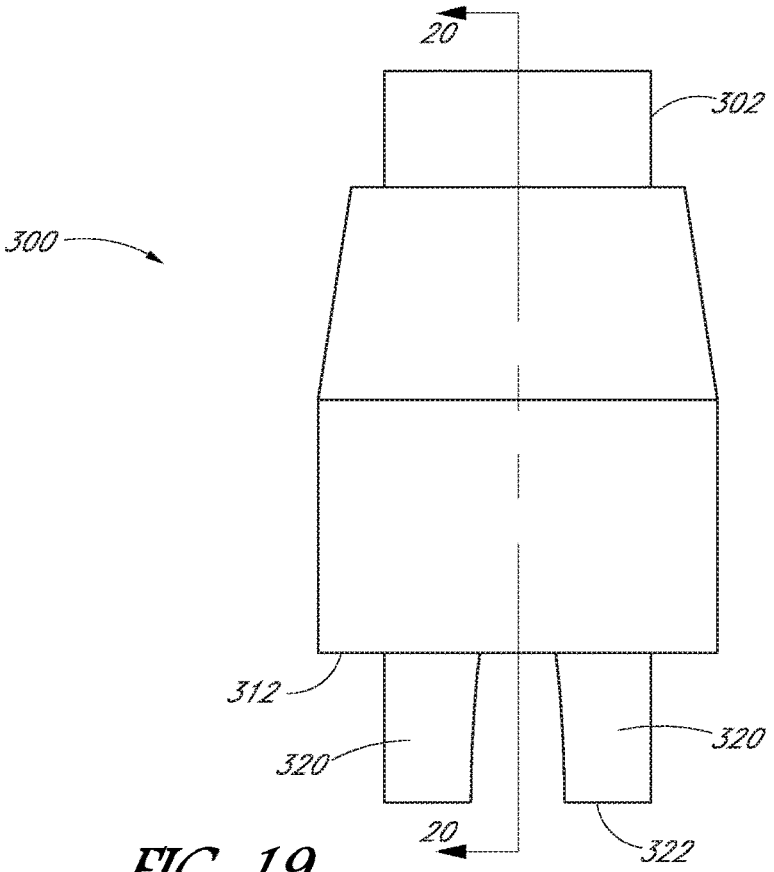
FIG. 19 is a side view of an inflow body of the personal vaporizer of FIG. 10.
Figure 20:
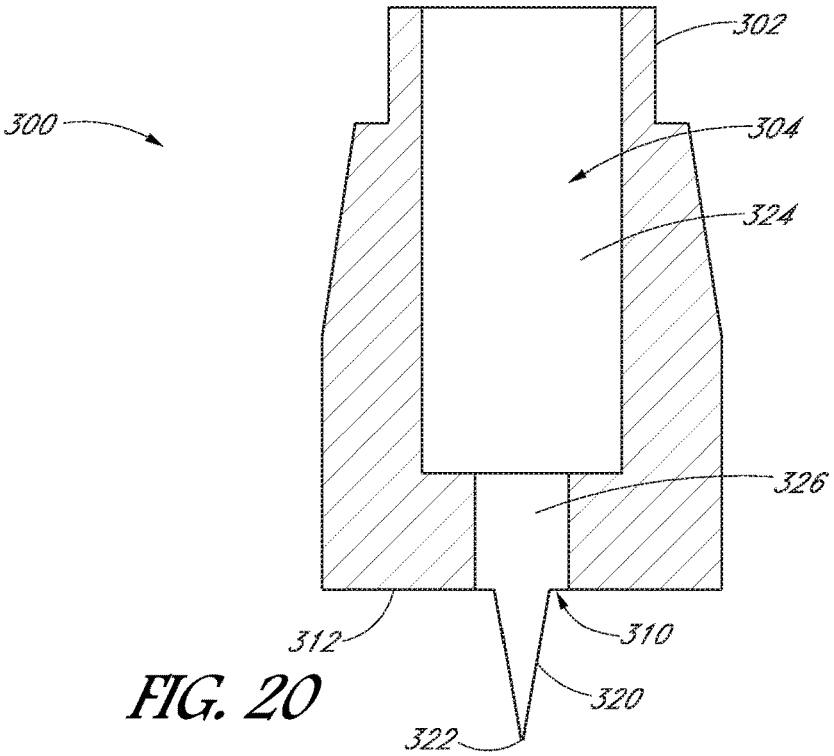
FIG. 20 is a cross-sectional view of the inflow body of FIG. 19 taken along lines 20-20.

With additional reference to FIGS. 19 and 20, an elongated flow director 300 includes a stepped proximal end 302 configured to be received into the receiver 286 of the inlet center space 284. In the illustrated embodiment, the flow director 300 is press-fit into the receiver 286. In other embodiments the flow director could be threaded, adhered, or otherwise connected to the flow body. A delivery passage 304 is defined within the flow director 300 and extends from the proximal end 302 to a downstream opening 310 formed through a distal wall 312. The delivery passage 304 communicates with the inlet center space 284 and extends along the axis of the vaporizer 200. A pair of tabs 320 extend distally from the distal wall 312 of the flow director 300. In the illustrated embodiment one of the tabs 320 is disposed on each side of the downstream opening 310 of the delivery passage 304 so that the tabs 320 straddle the downstream opening 310. In the illustrated embodiment, each tab 320 has a generally triangular shape in cross-section, terminating at an acute-angled distal edge 322.

In the illustrated embodiment, an upstream portion 324 of the delivery passage 304 has a greater diameter than a downstream portion 326 of the delivery passage 304. In some embodiments, the cross-sectional area of the upstream portion 324 of the delivery passage is about the same as the collective cross-sectional area of the inlet passages 282. However the cross-sectional area of the downstream portion 326 of the delivery passage 304 is substantially less than the collective cross-sectional area of the inlet passages 282.

Figure 22:
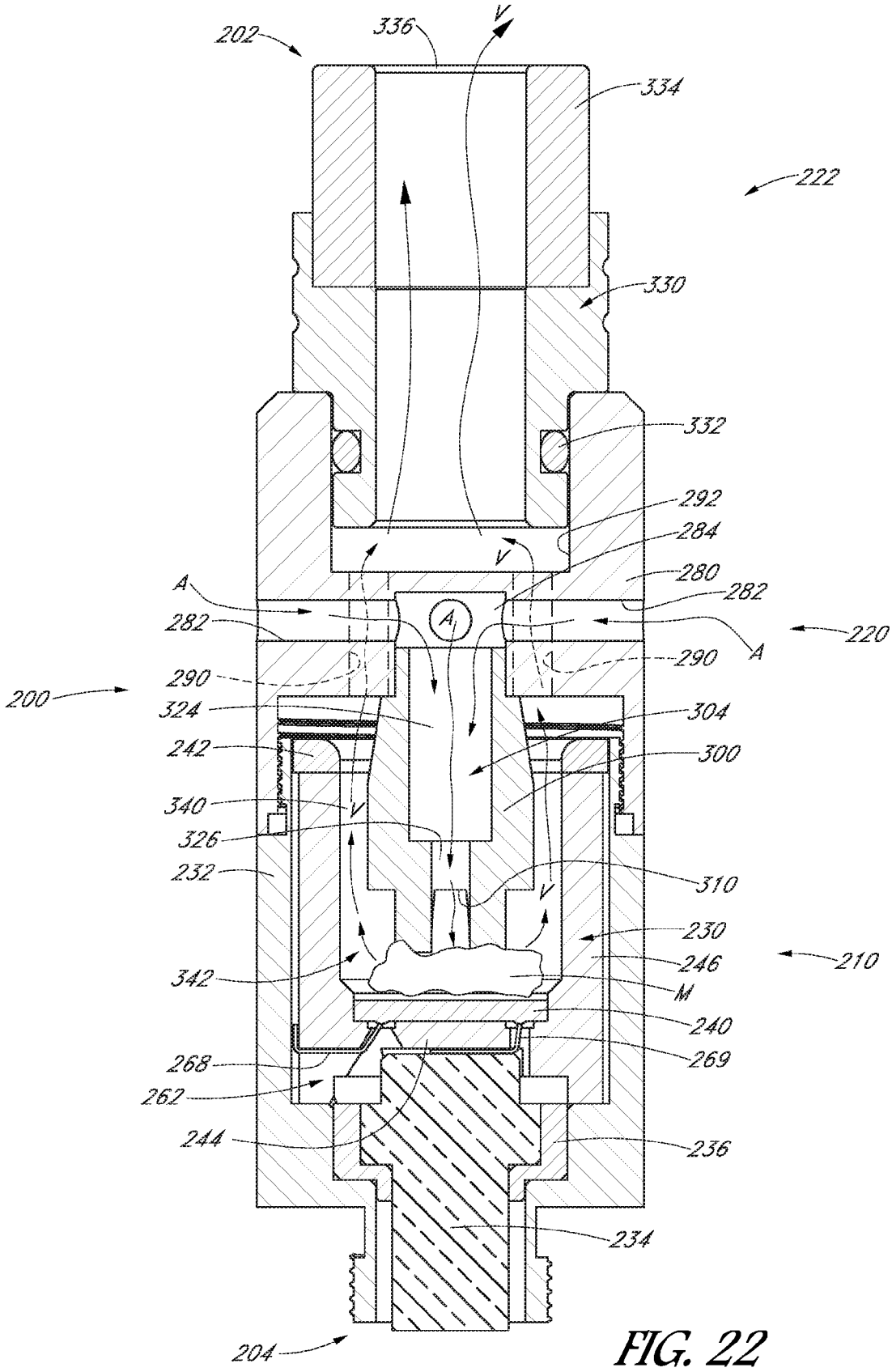
FIG. 22 is a cross-sectional view of the personal vaporizer of FIG. 10 taken along lines 22-22.

With additional reference to FIGS. 11 and 22, a mouthpiece base 330 is received into the mouthpiece receiver 292, and sealingly secured therein with the assistance of a sealing O-ring 332. A mouthpiece 334 is received and held within the mouthpiece base 330. The mouthpiece defines an outlet 336.

Figure 21:
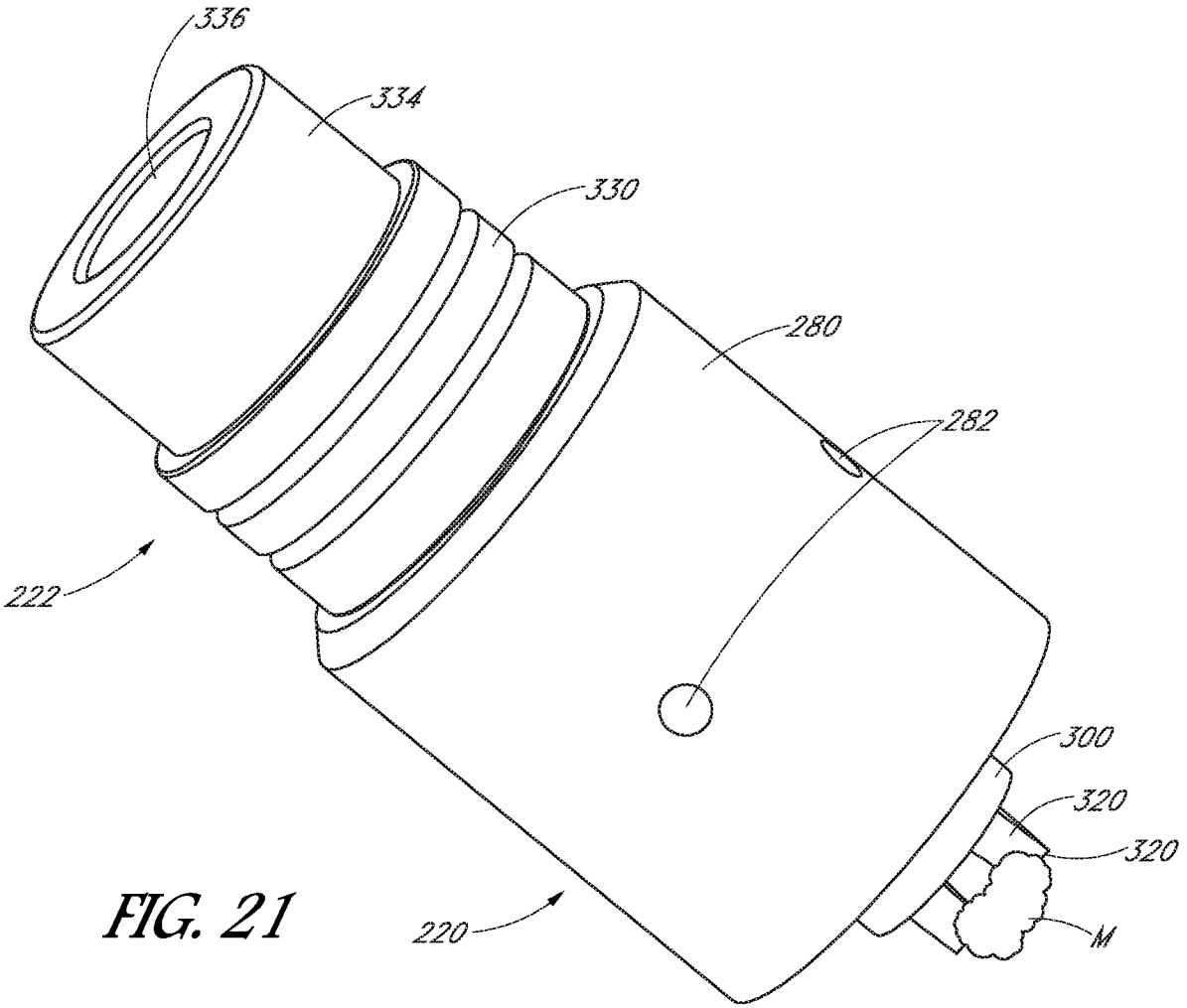
FIG. 21 is a perspective view of the airflow module of the personal vaporizer of FIG. 10.

With particular reference to FIG. 21, when the flow module 220 and mouthpiece module 222 are assembled, they comprise a flow assembly that can easily be detached from the atomizer module 210. As shown, the flow director 300, and particularly the flow director tabs 320, extend distally outwardly from the flow body 280. As such, the user may disconnect the flow assembly from the atomizer module and, using a scooping action, apply a medium M, such as a wax, onto the tabs 320 without using an external implement such as a spoon or the user's own fingers. The flow assembly can then be reattached to the atomizer module by threading the flow body onto the atomizer casing.

With reference next to FIG. 22, the flow director 300 and atomizer cup 230 preferably are configured so that, when assembled as shown, the distal edges 322 of the tabs 320 are immediately proximal of the heating element 240 within the atomizer cup 230. In this manner, medium M that has been scooped with the tabs 320 is placed immediately adjacent the heating element 240, and in prime position for atomization by the heating element. Also, the outer diameter of the flow director 300 is less than an inner diameter of the atomizer cup 230 so that an exit space 340 is defined between the flow director 300 and the atomizer cup side wall 246. A vaporizing chamber 342 is defined between the flow director distal wall 312 and the heating element 240. As such, in the illustrated embodiment, the downstream opening 310 opens into a center of the vaporizing chamber 342, along the axis of the vaporizer 200, and the exit space 340 is aligned with the radially outermost portion of the vaporizing chamber 342.

With continued reference to FIG. 22, during use, the user actuates delivery of current through the heating element 240 to atomize the medium M, and also draws a breath through the mouthpiece 334. As such, ambient air A is drawn into and through the inlet passages 282 into the inlet center space 284, from which it is directed into and through the delivery passage 304. Due to the reduced cross-sectional area of the downstream portion 326 of the delivery passage 304, intake air A is accelerated significantly when moving through the delivery passage 304. Also, as the tabs 320 straddle the downstream opening 310, this accelerated intake air A directly impacts the vaporizing medium M, which is simultaneously being atomized by the heating element 240.

Due to being redirected by the medium M and/or contact with the heating element 240, the accelerated air A tends to become turbulent just after entering the vaporizing chamber 342. Also, the airflow slows substantially after it enters within the vaporizing chamber 342, which has a cross-sectional flow area much greater than that of the downstream opening 310. Further, such air A is drawn radially outwardly to an outer edge of the vaporizing chamber 342, during which time atomized medium M becomes entrained in the air A, creating a high-quality vapor V. The vapor V is then drawn proximally through the exit space 340 and further proximally through the exit passages 290 of the flow body 280 into the mouthpiece receiver 292, from which it is drawn through the mouthpiece 334 and out of the mouthpiece outlet 336 to the user's mouth.

As shown, and as in other embodiments disclosed herein, intake air A is accelerated into the vaporizing chamber 342. Within the vaporizing chamber, the intake air will follow a flow path having dramatic direction changes. For example, the flow path within the vaporizing chamber 342 from the downstream opening 310 to and into the exit space 340 changes direction by 180°. Also, flow path velocity slows substantially within the vaporizing chamber 342.

Embodiments disclosed herein have been shown with generally circular cross-sections. It is to be understood, however, that other embodiments may employ the concepts and aspects described herein but have different cross-sectional shapes. For example, vaporizers having square or rectangular cross-sectional shapes may advantageously employ the aspects described in the embodiments disclosed in this specification.

The embodiments discussed above have disclosed structures with substantial specificity. This has provided a good context for disclosing and discussing inventive subject matter. However, it is to be understood that other embodiments may employ different specific structural shapes and interactions, and may employ various combinations of aspects discussed in the above embodiments.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. For example, structure or resembling the tabs in FIG. 22 may be used in embodiments such as are discussed in conjunction with FIGS. 1-6, 7, 8 and 9, and the embodiment discussed in connection with FIGS. 10-22 may be modified to incorporate one or more aspects described in connection with other embodiments. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

[1. A personal vaporizer having a distal end and a proximal end, a distal direction defined moving axially from the proximal end toward the distal end, a proximal direction being opposite the distal direction, comprising:

an atomizer module comprising an atomizer cup having a distal wall and a side wall extending in the proximal direction from the distal wall to a proximal edge, a heating element being arranged in or adjacent the atomizer cup, the cup being configured to accept a vaporizing medium so that the vaporizing medium is atomized when the heating element is energized;

a vaporizing chamber defined in part by the distal and side walls of the atomizer cup, the vaporizing medium being contained within the vaporizing chamber;

a flow body selectively attachable to a proximal side of the atomizer module, the flow body comprising an inlet passage through a side of the flow body, the inlet passage communicating with a delivery passage that extends in the distal direction from the inlet passage to a delivery opening, the delivery passage and delivery opening being defined by the flow body, the delivery opening being distal of the inlet passage and proximal of the vaporizing chamber, and being configured to direct intake air into the vaporizing chamber;

an exit passage communicating with the vaporizing chamber and defined by the flow body adjacent the delivery passage, and an exit opening communicating with the exit passage and being proximal of the vaporizing chamber; and a mouthpiece having a mouthpiece outlet that is in communication with the exit passage, the mouthpiece being proximal of the flow body;

wherein a vaporizing chamber flow path is defined within the vaporizing chamber between the delivery opening and the exit passage, and atomized vaporizing medium becomes entrained in the air flowing along the vaporizing chamber flow path so as to form a vapor; and wherein the vaporizer is configured so that as air is drawn out of the mouthpiece outlet, air is drawn in through the inlet passage and flows along the vaporizing chamber flow path.]

[2. A personal vaporizer as in claim 1, wherein the exit opening is proximal of the delivery opening.]

[3. A personal vaporizer as in claim 2, wherein the delivery opening is distal of the atomizer cup proximal edge.]

[4. A personal vaporizer as in claim 3, wherein the flow body has a distal wall, and the delivery opening is formed through the distal wall, and the vaporizing chamber is defined by the distal and side walls of the atomizer cup and by the distal wall of the flow body.]

[5. A personal vaporizer as in claim 2, wherein a cross-sectional area of the vaporizing chamber increases along the vaporizing chamber flow path.]

[6. A personal vaporizer as in claim 5, wherein delivery of air is accelerated and directed toward the distal wall of the atomizer cup and imparts turbulent flow characteristics to the accelerated air.]

[7. A personal vaporizer as in claim 2 additionally comprising a distal vapor chamber distal of the atomizer cup, and a vapor tube extending proximally from the distal vapor chamber to a mouthpiece.]

[8. A personal vaporizer as in claim 7, wherein a cross-sectional area of the delivery passage decreases moving distally along its length so that air flowing distally through the delivery passage is accelerated.]

[9. A personal vaporizer as in claim 1 additionally comprising an exit groove formed in the side wall of the atomizer cup, the exit opening communicating with the exit groove, and wherein the vapor flows distally through the exit groove.]

[10. A personal vaporizer as in claim 1, wherein the delivery opening directs a flow of air towards a center of the atomizer cup distal wall, and wherein the exit opening is radially spaced from the center of the atomizer cup.]

[11. A personal vaporizer as in claim 1, wherein the delivery opening directs a flow of air towards a first side of the atomizer cup, and wherein the exit opening is at or adjacent a second side of the atomizer cup generally opposite the first side.]

[12. A personal vaporizer as in claim 1, comprising a flow director extending distally beyond the distal end of the flow body and additionally comprising a tab extending distally from a distal wall of the flow director.]

[13. A personal vaporizer as in claim 1, wherein the flow body has a distal wall, and the vaporizing chamber is defined by the distal and side walls of the atomizer cup and by the distal wall of the flow body.]

[14. A personal vaporizer as in claim 1, wherein the flow body is movable as a unit.]

[15. A personal vaporizer as in claim 14, wherein the mouthpiece is selectively detachable from the flow body.]

[16. A personal vaporizer as in claim 14, wherein the delivery opening of the flow body is distal of the atomizer cup proximal edge.]

[17. A personal vaporizer as in claim 14, wherein a cross-sectional area of the delivery opening is less than a cross-sectional area of the inlet passage so that intake air is accelerated moving distally through the delivery passage and delivery opening prior to entering the vaporizing chamber and prior to contacting vaporizing medium.]

[18. A personal vaporizer as in claim 17, wherein the vaporizing chamber flow path changes direction between the delivery opening and the exit opening from being distally-directed to being proximally-directed.]

[19. A personal vaporizer, comprising:

an atomizer module comprising an atomizer cup having a distal wall and a side wall extending from the distal wall to a proximal edge, a heating element being arranged in or adjacent the atomizer cup, the cup being configured to accept a vaporizing medium so that the vaporizing medium is atomized when the heating element is energized;

a vaporizing chamber defined in part by the distal and side walls of the atomizer cup, the vaporizing medium being contained within the vaporizing chamber;

a flow body selectively attachable to the atomizer module, the flow body comprising an inlet passage through a side of the flow body, the inlet passage communicating with a delivery passage that extends distally to a delivery opening, the delivery opening being distal of the inlet passage and proximal of the vaporizing chamber, and being configured to direct intake air into the vaporizing chamber toward the distal wall;

an exit passage communicating with the vaporizing chamber and extending through the flow body, and an exit opening communicating with the exit passage and being proximal of the vaporizing chamber; and a mouthpiece having a mouthpiece outlet that is in communication with the exit passage;

wherein a vaporizing chamber flow path is defined between the delivery opening and the exit passage, intake air directed into the vaporizing chamber is redirected by the distal wall or vaporizing medium to become turbulent, and atomized vaporizing medium becomes entrained in the turbulent air flowing along the vaporizing chamber flow path so as to form a vapor;

wherein a cross-sectional area of the delivery opening is less than a cross-sectional area of the inlet passage so that intake air is accelerated moving distally through the delivery passage and delivery opening prior to entering the vaporizing chamber and prior to contacting vaporizing medium;

wherein the vaporizer is configured so that as air is drawn out of the mouthpiece outlet, air is drawn in through the inlet passage and flows along the vaporizing chamber flow path; and wherein the vaporizing chamber flow path changes direction from being distally-directed to being proximally-directed between the delivery opening and the exit opening.]

[20. A personal vaporizer as in claim 19, wherein the delivery opening is distal of the exit opening.]

[21. A personal vaporizer as in claim 19, wherein the flow body has a distal wall, and the vaporizing chamber is defined by the distal and side walls of the atomizer cup and by the distal wall of the flow body.]

[22. A personal vaporizer as in claim 21, wherein the distal wall of the flow body is distal of the atomizer cup proximal edge.]

[23. A personal vaporizer as in claim 19, wherein the vaporizing chamber has a cross-sectional flow area greater than a cross-sectional area of the delivery opening.]

[24. A personal vaporizer as in claim 23, wherein intake air that was accelerated moving distally through the delivery passage and delivery opening slows moving through the vaporizing chamber along the vaporizing chamber flow path.]

[25. A personal vaporizer as in claim 24, wherein the delivery passage has an upstream portion and a downstream portion, and wherein a cross-sectional area of the downstream portion is less than a cross-sectional area of the upstream portion.]

[26. A personal vaporizer as in claim 24, wherein the heating element is contained within the vaporizing chamber, and wherein accelerated intake air is directed from the delivery opening towards the heating element within the vaporizing chamber, and the intake air becomes turbulent within the vaporizing chamber.]

[27. A personal vaporizer as in claim 24, wherein the vaporizing chamber flow path comprises a radially-directed portion between a distally-directed portion and a proximally-directed portion, and flow is turbulent within the radially-directed portion.]

[28. A personal vaporizer as in claim 27, wherein vaporizing medium being heated by the heating element is interposed in the radially-directed portion.]

[29. A personal vaporizer, comprising:

an atomizer module comprising an atomizer cup having a distal wall and a side wall extending from the distal wall to a proximal edge, a heating element being arranged in or adjacent the atomizer cup, the cup being configured to accept a vaporizing medium so that the vaporizing medium is atomized when the heating element is energized;

a vaporizing chamber defined in part by the distal and side walls of the atomizer cup;

a flow body selectively attachable to the atomizer module, the flow body comprising an inlet passage through a side of the flow body, the inlet passage communicating with a delivery passage that extends distally to a delivery opening, the delivery opening being distal of the inlet passage and being configured to direct intake air into the vaporizing chamber;

a flow director extending distally beyond the distal end of the flow body and additionally comprising a tab extending distally from a distal wall of the flow director, the delivery passage being defined within the flow director, and the delivery opening is defined through the distal wall of the flow director;

an exit passage communicating with the vaporizing chamber and extending through the flow body, and an exit opening communicating with the exit passage and being radially spaced from the delivery opening; and a mouthpiece having a mouthpiece outlet that is in communication with the exit passage;

wherein a vaporizing chamber flow path is defined between the delivery opening and the exit passage, and atomized vaporizing medium becomes entrained in the air flowing along the vaporizing chamber flow path so as to form a vapor; and wherein the vaporizer is configured so that as air is drawn out of the mouthpiece outlet, air is drawn in through the inlet passage and flows along the vaporizing chamber flow path.]

[30. A personal vaporizer as in claim 29, wherein the tab is disposed adjacent the delivery opening.]

[31. A personal vaporizer as in claim 30, wherein a distal edge of the tab is disposed adjacent the heating element in the vaporizing chamber.]

[32. A personal vaporizer as in claim 30, additionally comprising a second tab extending distally from the distal wall of the flow director, wherein the second tab is disposed adjacent the delivery opening on a side of the delivery opening opposite the tab.]

*33. A personal vaporizer having a first end and a second end, a first direction defined moving from the second end toward the first end, a second direction being opposite the first direction, comprising:*

*an atomizer comprising a vaporizing chamber having an end wall and a side wall extending in the first direction from the end wall to an open end, a heating element being arranged in or adjacent the vaporizing chamber, the heating element configured to atomize a vaporizing medium contained in the vaporizing chamber when the heating element is energized;*

*the vaporizing chamber configured to receive a flow of intake air moving in the second direction through the vaporizing chamber open end;*

*the vaporizing chamber configured so that when the heating element is energized, vaporizing medium in the vaporizing chamber is atomized and intake air is mixed with atomized vaporizing medium in the vaporizing chamber to form a vapor; and*

*a vaporizing chamber vapor path defined within the vaporizing chamber and extending in the first direction toward the open end;*

*an outer vapor flow path defined radially-spaced from the vaporizing chamber and in communication with the vaporizing chamber vapor path; and*

*a mouthpiece having a mouthpiece outlet that is in communication with the outer vapor flow path.*

*34. The personal vaporizer of claim 33, wherein the outer vapor path is configured to conduct vapor in the second direction past the atomizer cup.*

*35. The personal vaporizer of claim 33, wherein the outer vapor path is configured to conduct vapor in the second direction.*

*36. The personal vaporizer of claim 35, comprising a housing supporting the vaporizing chamber and having a housing open end, a space defined between the housing open end and the vaporizing chamber open end.*

*37. The personal vaporizer of claim 36, wherein a radial vapor flow path is defined in the space, and wherein the radial flow path connects the vaporizing chamber vapor path to the outer vapor path.*

*38. The personal vaporizer of claim 33, wherein the outer vapor flow path extends in the second direction adjacent the side wall of the vaporizing chamber and past the end wall of the vaporizing chamber to a bottom vapor chamber.*

*39. The personal vaporizer of claim 38, additionally comprising a bottom radially-extending flow path defined by the bottom vapor chamber.*

*40. The personal vaporizer of claim 39, additionally comprising a vapor tube radially offset from the outer vapor flow path and having an upstream end communicating with the bottom radially-extending flow path.*

*41. The personal vaporizer of claim 40, wherein the vapor tube comprises a downstream end, and a vapor tube path is defined moving in the first direction from the upstream end to the downstream end.*

*42. A personal vaporizer, comprising:*

*an atomizer comprising a cup having a bottom wall and a side wall extending upwardly from the bottom wall to an open end, a vaporizing chamber being defined within the cup, the cup adapted to receive a vaporizing medium within the vaporizing chamber, a heating element being arranged in or adjacent the cup;*

*a housing supporting the cup, the housing having an open end and defining a delivery passage extending from the housing open end to the cup open end, the delivery passage configured to conduct intake air therethrough in a first longitudinal direction to and through the open end of the cup; and*

*a mouthpiece having a mouthpiece outlet;*

*wherein the vaporizing chamber is configured so that when the heating element is energized, vaporizing medium contained within the vaporizing chamber is atomized and intake air is mixed with atomized vaporizing medium in the vaporizing chamber to form a vapor; and*

*a chamber vapor flow path is defined in the vaporizing chamber and is directed in a second longitudinal direction generally opposite the first longitudinal direction, the chamber vapor flow path being radially offset from the elongated delivery passage; and*

*wherein the vapor flow path is configured to conduct vapor out of the vaporizing chamber; and*

*a second vapor flow path defined between the cup side wall and the housing, wherein the second vapor flow path is configured to receive vapor from the chamber vapor flow path and conduct vapor in the first longitudinal direction, the second vapor flow path communicating with the mouthpiece outlet.*

*43. The personal vaporizer of claim 42, wherein a space is defined between a top edge portion of the cup and the housing open end, and a first radial vapor flow path is defined in the space, wherein the first radial vapor flow path connects the chamber vapor flow path to the second vapor flow path.*

*44. The personal vaporizer of claim 43, wherein the top edge portion of the cup defines the open end of the cup.*

*45. The personal vaporizer of claim 42, wherein the second vapor flow path extends in the first longitudinal direction past the cup bottom wall to a point vertically below the cup bottom wall.*

*46. The personal vaporizer of claim 45, additionally comprising a vapor tube radially offset from the second vapor flow path, an upstream end of the vapor tube being vertically lower than the cup bottom wall, a downstream end of the vapor tube being vertically higher than the cup open end, the vapor tube defining a vapor tube flow path configured to receive vapor from the second vapor flow path and communicate the vapor in the second longitudinal direction.*

*47. The personal vaporizer of claim 46, additionally comprising a second radial vapor flow path vertically lower than the cup bottom wall, the second radial vapor flow path configured to communicate vapor from the second vapor flow path to the vapor tube flow path.*

*48. The personal vaporizer of claim 47, comprising a bottom chamber vertically below the cup bottom wall, the second radial vapor flow path being defined by the bottom chamber.*

*49. The personal vaporizer of claim 46, wherein the vapor tube flow path is radially spaced from the delivery passage.*

*50. The personal vaporizer of claim 49, wherein a downstream end of the vapor tube is vertically higher than the cup open end, and the vapor tube defines a vapor tube flow path configured to receive vapor from the second vapor flow path and communicate the vapor in the second longitudinal direction.*

*51. The personal vaporizer of claim 45, comprising a bottom chamber vertically below the cup bottom wall, the second vapor flow path communicating with the bottom chamber.*

* * * * *